(12) United States Patent
Kamei

(10) Patent No.: US 11,331,511 B2
(45) Date of Patent: May 17, 2022

(54) HEAD PHOTIC STIMULATION DEVICE, HEAD PHOTIC STIMULATION METHOD, AND PROGRAM

(71) Applicant: NAGASAKI METHOD & CO., LTD., Izumo (JP)

(72) Inventor: Tsutomu Kamei, Kumagaya (JP)

(73) Assignee: NAGASAKI METHOD & CO., LTD., Izumo (JP)

( * ) Notice: Subject to any disclaimer, the term of this patent is extended or adjusted under 35 U.S.C. 154(b) by 38 days.

(21) Appl. No.: 16/316,898

(22) PCT Filed: Aug. 5, 2016

(86) PCT No.: PCT/JP2016/073194
§ 371 (c)(1),
(2) Date: Jan. 10, 2019

(87) PCT Pub. No.: WO2018/025419
PCT Pub. Date: Feb. 8, 2018

(65) Prior Publication Data
US 2019/0299021 A1    Oct. 3, 2019

(51) Int. Cl.
*A61N 5/00* (2006.01)
*A61N 5/06* (2006.01)

(52) U.S. Cl.
CPC ........ *A61N 5/06* (2013.01); *A61N 2005/0647* (2013.01); *A61N 2005/0651* (2013.01);
(Continued)

(58) Field of Classification Search
CPC .......................... A61N 5/06; A61N 2005/0647
See application file for complete search history.

(56) References Cited

U.S. PATENT DOCUMENTS 5,241,967 A * 9/1993 Yasushi ................. A61B 5/378
                                                                    600/545
5,769,878 A    6/1998 Kamei
(Continued)

FOREIGN PATENT DOCUMENTS

EP      0375106 A1    6/1990
EP      0736307 A2    10/1996
(Continued)

OTHER PUBLICATIONS

European Search Report corresponding to EP Application No. 16911678.7, dated Nov. 20, 2019 (4 pages).
(Continued)

*Primary Examiner* — Gary Jackson
*Assistant Examiner* — Anant A Gupta
(74) *Attorney, Agent, or Firm* — Lucas & Mercanti, LLP

(57) ABSTRACT

Provided is a head photic stimulation device including: a brain wave amplifier which subjects the subject brain waves acquired using a brain wave sensor to A/D conversion and amplification; a control signal generation circuit which, based on an output signal from the brain wave amplifier, generates a control signal for controlling LED driving; and a light irradiation unit which is driven based on an output from the control signal generation circuit, and which includes an LED for irradiating a head. The control signal generation circuit includes a band-pass filter for filtering an input signal, a DSP (signal processing) unit for controlling a signal that has passed through the band-pass filter, and a light irradiation output unit using a near-infrared LED for irradiating the head. The DSP unit has a feedback function for matching a phase of a PWM output for controlling the light irradiation output unit, in synchronism with the subject brain waves.

4 Claims, 18 Drawing Sheets

(52) U.S. Cl.
CPC ............... *A61N 2005/0659* (2013.01); *A61N 2005/0667* (2013.01)

(56) References Cited

U.S. PATENT DOCUMENTS

| | | |
|---|---|---|
| 6,129,748 A | 10/2000 | Kamei |
| 6,537,301 B1 | 3/2003 | Kamei |
| 2003/0181961 A1 | 9/2003 | Kamei |
| 2009/0149770 A1* | 6/2009 | Sing .................. A61B 5/04017 600/544 |
| 2010/0016783 A1* | 1/2010 | Bourke, Jr. ............ A61P 17/02 604/20 |
| 2010/0324631 A1 | 12/2010 | Tass et al. |
| 2013/0066404 A1* | 3/2013 | Tapper ................. A61N 5/0616 607/90 |
| 2015/0342493 A1* | 12/2015 | Hardt .................. A61B 5/7455 600/545 |
| 2017/0304587 A1* | 10/2017 | Santostasi ........... A61B 5/4857 |

FOREIGN PATENT DOCUMENTS

| | | |
|---|---|---|
| JP | H02-168934 A | 6/1990 |
| JP | H09-84888 A | 3/1997 |
| JP | 2001-231871 A | 8/2001 |
| JP | 2002-035130 A | 2/2002 |

OTHER PUBLICATIONS

Kasper et al., "Immunological correlates of seasonal fluctuations in mood and behavior and their relationship to phototherapy," Psychiatry Res., vol. 36, pp. 253-264 (1991).

Terman et al., "Light therapy for seasonal affective disorder: a review of efficacy", Neuropsychopharmacol., vol. 2, pp. 1-22 (1989).

Japanese Patent Office, Japanese Office Action dated Dec. 16, 2020, which was issued in connection with Japanese Patent Application No. 2018-531726 (4 pages).

* cited by examiner (a) Original brain waves (waveform 1))

(b) BPF 1 output (waveform 2))

(c) AGC output limiter output (waveform 3))

(d) BPF 2 output (waveform 4))

(a)

(b)

(c)

(d)

HEAD PHOTIC STIMULATION DEVICE, HEAD PHOTIC STIMULATION METHOD, AND PROGRAM

CROSS-REFERENCE TO RELATED APPLICATIONS

This application is a 371 of PCT/JP2016/073194, filed Aug. 5, 2016.

TECHNICAL FIELD

The present invention relates to a photic stimulation technology, and more particularly to a technology for photic stimulation of a head.

BACKGROUND ART

As an example of what a change in the light environment in nature brings to the immune system of a living organism, it has been reported (see Non Patent Literature 1 indicated below) that the degree of unpleasant mood or behavioral disorder caused by a decrease in the hours of sunlight in autumn or winter is negatively correlated with the number of natural killer cells (hereafter NK cells) in the peripheral blood. The report suggests the possibility that continuous light, such as sunlight during the daytime, may be useful for immune regulation. With respect to a reaction of light in the living organism, it is said that in birds, reptiles, and fish, light passes through the skull and directly reacts with light-sensitive pineal cells, in addition to travelling along the optic pathway. With respect to humans, no such reaction outside the optic pathway is known.

Focusing on the medical benefits of light including light in nature or otherwise, medium-wavelength (UVB) or long-wavelength (UVA) ultraviolet radiation has so far been applied for the treatment of skin diseases such as psoriasis, vitiligo, and atopic dermatitis; bright light therapy has been applied for treating seasonal affective disorder (SAD), depression and the like. Near-red rays have been applied for the treatment of pain, skin ulcer and the like. Thus, light is being widely applied, particularly in clinical medicine. Medical reports on the use of diode light as a light source has so far included basic researches indicating the promotion of wound healing effects of near-red light emitting diode light. Thus, medical benefits of less invasive light sources are also being studied.

There have already been several reports on the study of the influence visible light has on immune response via the optic pathway, i.e., a nervous system. The inventors have previously reported that the stimulation of α-waves in the frontal region that is observed when a healthy subject is subjected to photic driving is correlated with the activation of cellular immunity in the peripheral blood.

However, light-driven photic stimulation through the eye poses a kind of physical stress to the subject, and has been thought to act against the enhancement of the immune system.

The inventor has also proposed a technology to non-invasively activate the brain and immune mechanism through light irradiation from forwardly of the frontal region with both eyes completely shielded from light (see Patent Documents 1 and 2).

Patent Document 1 discloses an irradiation tool provided with a light source portion that contacts the frontal region, and a band portion for mounting (fixing) the light source section onto the head of a user. The light source section has a number of LEDs arranged on the inner side (the frontal region side of the user) thereof. The light source section includes a lower edge portion and side edge portions that are fitted with light-shielding portions.

CITATION LIST

Patent Literature

Patent Literature 1: JP 2001-231871 A
Patent Literature 2: JP H09-84888 A

Non Patent Literature

Non Patent Literature 1: S. Kasper, N. E. Rosenthal, S. Barberi, A. Williams, Tamarkin L., S. L. B. Rogers and S. R. Pillemer: Immunological correlates of seasonal fluctuations in mood and behavior and their relationship to phototherapy, Psychiatry Res., 36, pp. 253-264 (1991), M. Terman, J. S. Terman, F. M. Quitkin, P. J. McGrath, J. W. Stewart and B. Rafferty: Light therapy for seasonal affective disorder: a review of efficacy, Neuropsychopharmacol., 2, pp. 1-22 (1989)

SUMMARY OF INVENTION

Technical Problem

However, the technology described in Patent Document 1 irradiates the head with uniform light, and the effect varies greatly among individuals.

An object of the present invention is to solve the above problem and to provide a photic stimulation technology suitable for each individual.

Another object of the present invention is to mitigate discomfort and the like upon initial introduction.

Solution to Problem

According to an aspect of the present invention, there is provided a head photic stimulation device including: a brain wave amplifier which subjects the subject brain waves acquired using a brain wave sensor to A/D conversion and amplification; a control signal generation circuit which, based on an output signal from the brain wave amplifier, generates a control signal for controlling LED driving; and a light irradiation unit which is driven based on an output from the control signal generation circuit, and which includes an LED for irradiating a head. The control signal generation circuit includes a band-pass filter for filtering an input signal, a DSP (signal processing) unit for controlling a signal that has passed through the band-pass filter, and a light irradiation output unit using a near-infrared LED for irradiating the head. The DSP unit has a feedback function for matching a phase of a PWM output for controlling the light irradiation output unit, in synchronism with the subject brain waves.

Using the band-pass filter that passes the frequency band including a part of the θ-wave band and a part of the α-wave band makes it possible to perform a feedback that mitigates discomfort and the like upon initial introduction.

The DSP unit may include a band-pass filter (BPF) which passes a frequency band including a part of a θ-wave band and a part of an α-wave band; a phase-locked loop (PLL) for detecting a phase of an output signal from the band-pass filter; a fast Fourier transform (FFT) unit which accurately extracts a frequency of a maximum amplitude of the part of the θ-wave band and the part of the α-wave band; and a frequency/phase control unit which controls the frequency and the phase of an input signal from the FFT unit, and which performs a feedback to the PLL.

The frequency/phase control unit may synchronize an amplitude in alignment with a phase of input brain waves at the time of frequency switching.

The frequency/phase control unit, at the time of frequency switching, may extend time until an output phase becomes zero and, after an interval, perform synchronization in alignment with a zero point of a phase of input brain waves.

The FFT unit may extract, from the part of the θ-wave band and the part of the α-wave band, the frequency of the maximum amplitude of the brain waves in the bands using the band-pass filter and the FFT, and further calculate a moving average to increase accuracy.

Preferably, the PLL may include a phase comparator for comparing the phase of the input signal; a loop filter; and a VCO which receives an output of the loop filter as an input and feeds an output of the VCO back to the phase comparator.

While the phase of the brain waves is constantly tracked by the PLL and frequency varies, the frequency of the VCO of the PLL can be fixed by means of the control signal.

Preferably, the PLL may perform a switching interrupt (pause) at a timing $t_1$, continue oscillation until a phase of the VCO reaches a zero-crossing point, determine whether the phase of the PLL is zero, and, if zero, start signal output of the PLL at a previous average frequency.

In this way, synchronization of the phase of the control signal to the near-infrared LED with the phase of the subject brain waves can be performed quickly.

According to another aspect of the present invention, there is provided a head photic stimulation method using a head photic stimulation device comprising a brain wave amplifier which subjects the subject brain waves acquired using a brain wave sensor to A/D conversion and amplification, a control signal generation circuit which, based on an output signal from the brain wave amplifier, generates a control signal for controlling LED driving, and a light irradiation unit which is driven based on an output from the control signal generation circuit, and which includes an LED for irradiating a head. The control signal generation circuit performs a band-pass filtering process of filtering an input signal, a DSP process of controlling a signal that has passed through the band-pass filter, and a light irradiation output process using a near-infrared LED for irradiating the head. The DSP process includes a feedback process of matching a phase of a PWM output for controlling the light irradiation output process, in synchronism with the subject brain waves.

The DSP step includes a band-pass filter (BPF) process of passing a frequency band including a part of a θ-wave band and a part of an α-wave band; a phase-locked loop (PLL) process of detecting a phase of an output signal of the band-pass filtering process; a fast Fourier transform (FFT) process of accurately extracting a frequency of a maximum amplitude of the part of the θ-wave band and the part of the α-wave band; and a frequency/phase control process of controlling the frequency and the phase of an input signal from the FFT process, and performing a feedback in the PLL process.

The present invention may provide a program for causing a computer to perform the head photic stimulation method according to claim 8 or 9, and may also provide a computer-readable recording medium having the program recorded thereon.

Advantageous Effects of Invention

According to the present invention, a photic stimulation technology suitable for each individual can be provided.

According to the present invention, a feedback that mitigates discomfort and the like upon initial introduction can be performed.

DESCRIPTION OF EMBODIMENTS

Figure 1A:
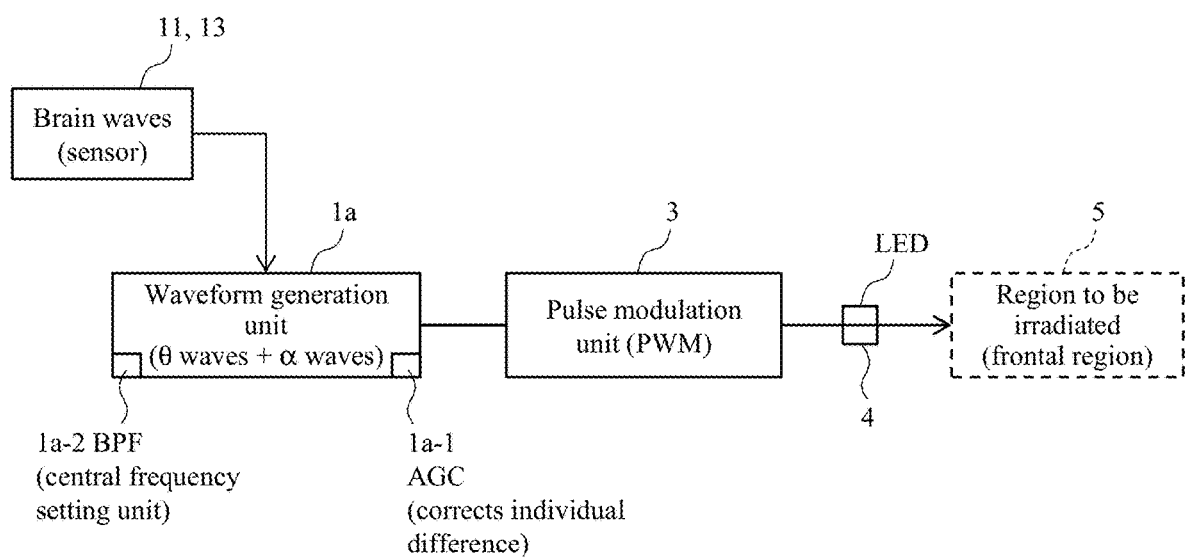
FIG. 1A is a functional block diagram illustrating a configuration example of a photic stimulation device according to a first embodiment of the present invention.

In the following, embodiments of the present invention will be described with reference to the drawings. In the drawings, like reference numerals refer to like members unless otherwise indicated.

Western medicine has no concepts of "individual differences" or "predisposition". The inventor has been studying technology for effectively reviving functions that have degraded, taking individual differences and predisposition into consideration.

In particular, the inventor conceived of enhancing the amplitudes of α waves and θ waves being generated spontaneously, by automatically adjusted pulsed light irradiation of the head centered around the prefrontal area (frontal association area), on the basis of the rhythm of the unique brain waves of each individual, thereby non-invasively enhancing nervous impulse in the brain cortex, activating the living organism through changes in the endocrine system, and activating cellular immunity.

On the basis of the above conception, the embodiments of the present invention will be described.

First Embodiment

First, a photic stimulation device according to a first embodiment of the present invention will be described. In the present description, the head includes the prefrontal area (frontal association area) and refers to a head area excluding the occipital area.

FIG. 1A is a functional block diagram illustrating a configuration example of the photic stimulation device according to the first embodiment of the present invention. The function may be implemented using a hardware configuration, a software configuration, or a combination of both. The same holds true hereinafter.

Figure 2:
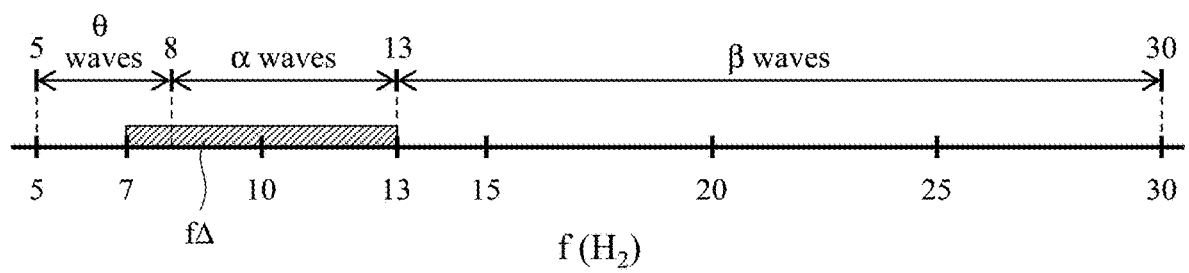
FIG. 2 is a diagram illustrating an example of a frequency band of brain waves utilized in the present embodiment.

FIG. 2 is a diagram for describing the frequency band of brain waves utilized in the present embodiment. Theta waves have a band of 5 to 8 Hz, α waves have a band of 8 to 13 Hz, and β waves have a band of 13 to 30 Hz.

As illustrated in FIG. 1A, the photic stimulation device in the present embodiment utilizes, on the basis of the brain waves of a subject acquired from a sensor 11 (a brain wave sensor 11 and a brain wave amplifier 13; hereinafter also referred to as the subject brain waves), for example, a part of θ waves and a part of α waves of the brain waves, such as the brain waves in a frequency band of 7 to 13 Hz illustrated in FIG. 2. The photic stimulation device according to the present embodiment, based on the brain waves of the frequency band, includes a waveform generation unit 1a which generates an appropriate waveform based on the subject brain waves, a pulse modulation unit 3 which subjects an output from the waveform generation unit 1a to pulse modulation (PWM modulation), and a light irradiation unit 4, such as a red light emitting diode (for example, an LED with a light emission wavelength of 660 nm), which is driven on the basis of a pulse-modulated drive waveform. Preferably, the wavelength of the light source for the red light in the light irradiation unit 4 is in a range of from 610 to 750 nm. Red pulsed light irradiated from the light irradiation unit 4 irradiates a region 5 to be irradiated, such as the head of the subject. While the waveform generation unit 1a has been described as generating an appropriate waveform on the basis of the subject brain waves, the object from which the waveform is generated is not limited to the subject brain waves. For example, it is also possible to utilize brain waves from a close relative or a patient with a similar disease.

The waveform generation unit 1a may include, for example, an AGC unit 1a-1 for suppressing differences in amplitude among individuals, and a BPF unit 1a-2 for only extracting the waveforms of predetermined frequency bands of α waves and θ waves. The detailed configurations of such units will be described in detail in the second embodiment.

Figure 3A:
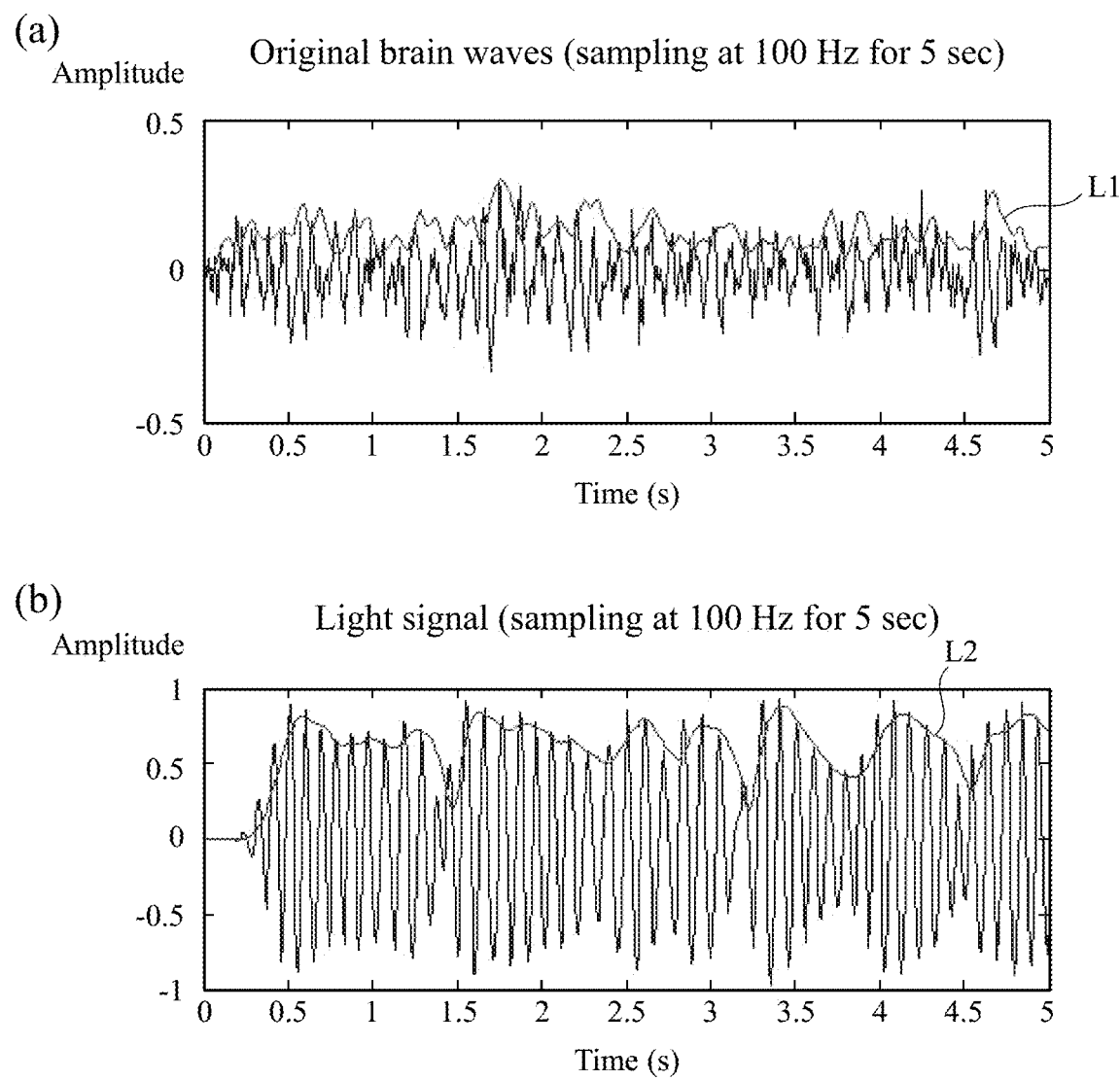
FIG. 3A illustrates examples of input and output waveforms in a fluctuating waveform generation unit illustrated in FIG. 1A.

FIG. 3A illustrates examples of an input signal of brain waves to the waveform generation unit 1a (original brain waves (a)) and an output signal (b) from the waveform generation unit 1a, in which the vertical axis shows amplitude and the horizontal axis shows time (s). In each case, sampling is performed at 100 Hz. L1 and L2 indicate the envelopes of the respective waveforms.

Figure 3B:
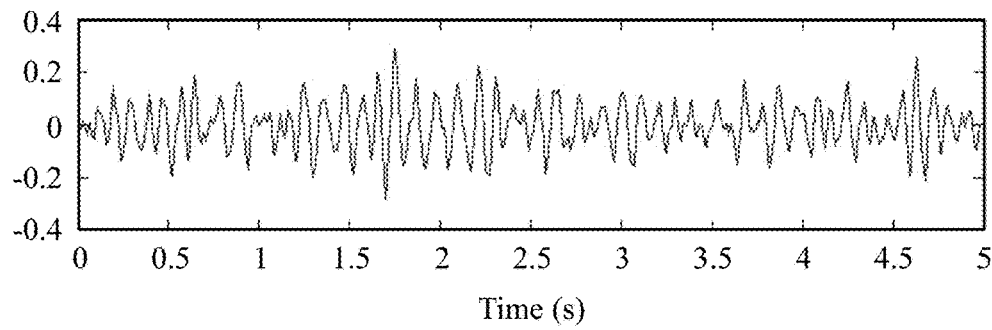
FIG. 3B illustrates an example of transition of waveform in the circuit illustrated in FIG. 1B.
Figure 3B:
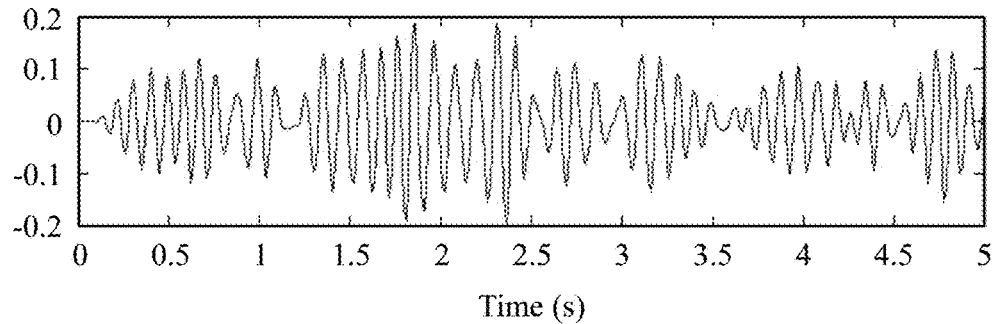
Figure 3B:
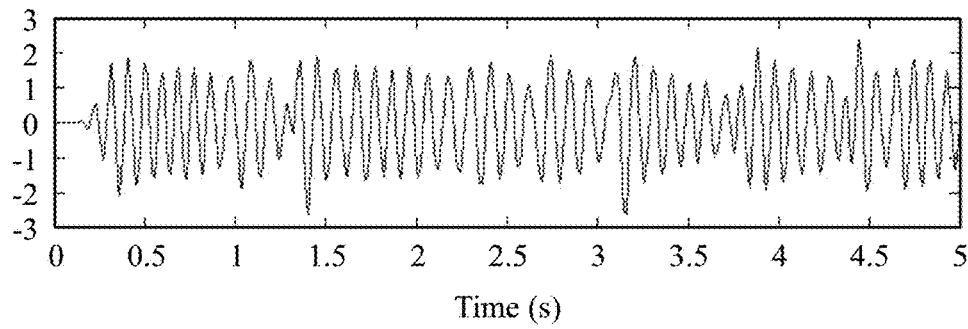
Figure 3B:
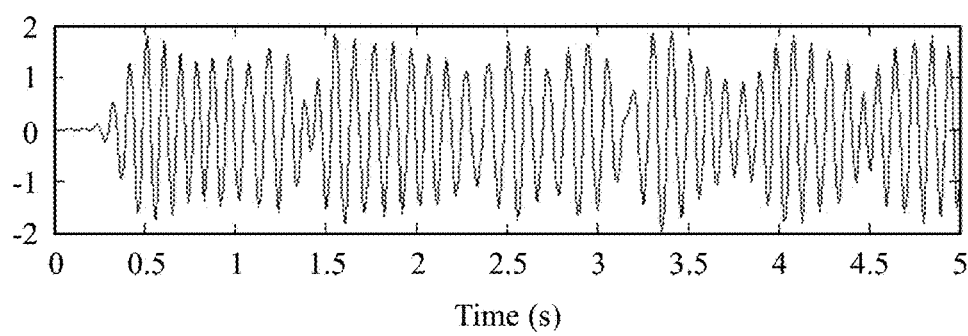

As illustrated in FIG. 3A and FIG. 3B, basically, a waveform modification process is performed such that singular points of the individual are absorbed (removed) while maintaining individual fluctuations, as will be seen from a comparison of the envelopes L1 and L2.

Thus, in the photic stimulation device according to the present embodiment, a waveform having frequency fluctuations based on the brain waves of the individual are prepared, the waveform is subjected to pulse modulation to generate a drive waveform, and the red LED is driven on the basis of the drive waveform to irradiate the head. Accordingly, it is possible to remove the singular points of the individual while taking the individual's characteristics into consideration, and to achieve, in a state in which heat generation is suppressed by pulse modulation, non-invasive enhancement of nervous impulse in the brain cortex, activation of the living organism due to a change in the endocrine system, and activation of cellular immunity.

The LED is not limited to a red LED, and the frequency band is not limited to from 7 to 13 Hz. Nor is the light source limited to one using an LED.

Second Embodiment

Figure 1B:
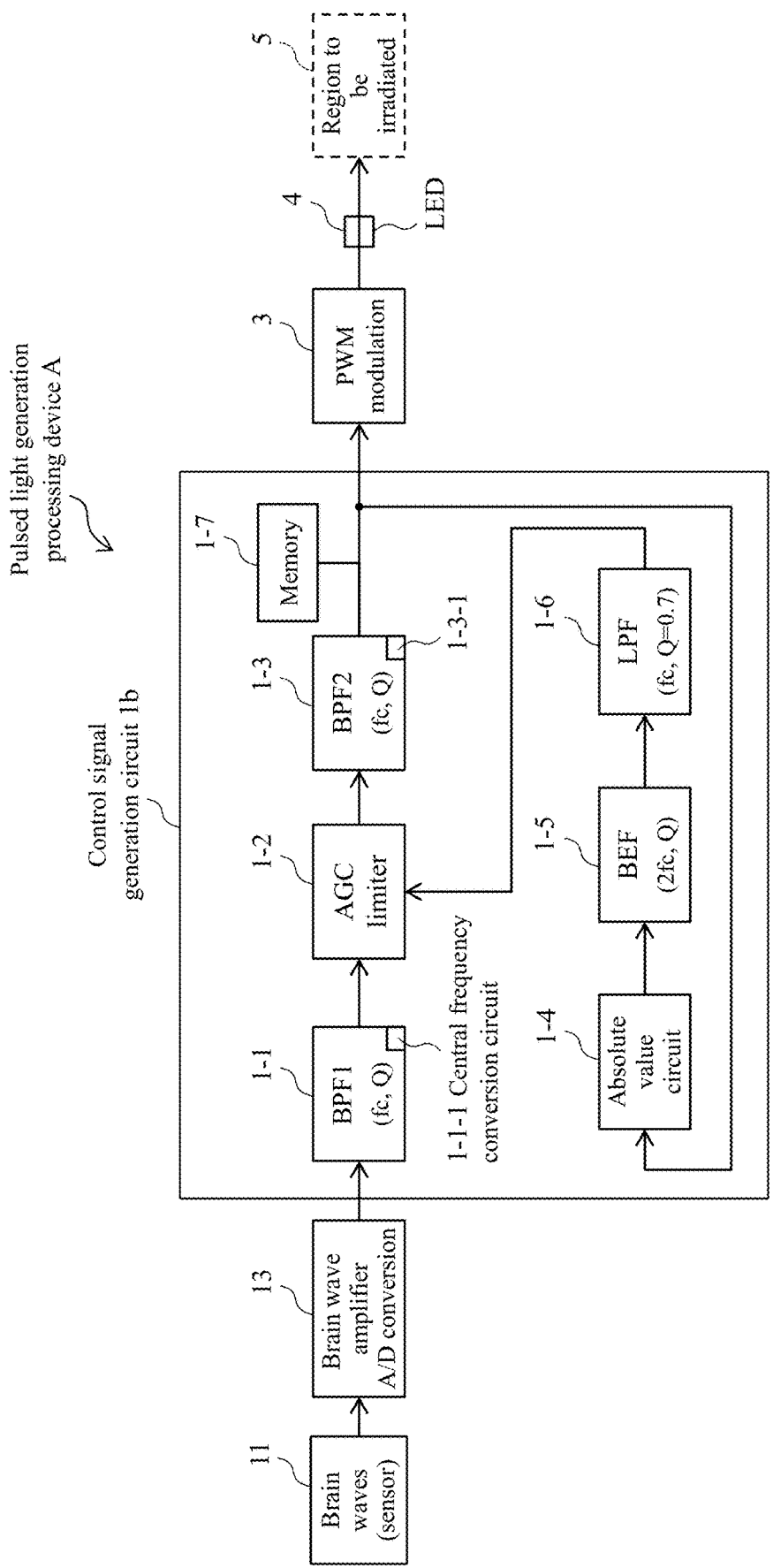
FIG. 1B is a functional block diagram illustrating a configuration example of a photic stimulation device according to a second embodiment of the present invention.

A second embodiment of the present invention will be described. FIG. 1B is a functional block diagram of a configuration example of the photic stimulation device according to the present embodiment, the diagram corresponding to FIG. 1A.

When a drive voltage for pulsed light is generated on the basis of the subject brain waves, if the photic stimulation is too strong, the body would be exposed to too strong a stimulation. If the photic stimulation is too weak, the effect would be too little.

As illustrated in FIG. 1B, the photic stimulation device according to the present embodiment is provided with: a brain wave amplifier 13 which subjects the brain waves of the subject acquired from the sensor 11 to A/D conversion, and amplification, as needed; a control signal generation circuit 1b which generates a control signal for controlling the driving of the LED on the basis of an output signal from the brain wave amplifier 13; a PWM modulation unit 3 which subjects an output from the control signal generation circuit 1b to PWM modulation; and a light irradiation unit 4 equipped with the red LED which is driven based on an output signal from the PWM modulation unit 3. Light from the light irradiation unit 4 irradiates the region 5 to be irradiated of the subject, such as the head, as pulsed light. The PWM modulation unit 3 expresses a waveform by means of variable pulse width and positive/negative signs, without changing the frequency. In this way, it becomes possible to reduce ripple components in output voltage and enhance response performance with respect to load variations. Instead of PWM modulation, PFM modulation may be used.

The control signal generation circuit 1b includes, for example, a first band-pass filter (BPF 1) 1-1, an AGC limiter 1-2, and a second band-pass filter (BPF 2) 1-3.

The control signal generation circuit 1b also includes, as a feedback function for feeding the output from the second band-pass filter (BPF 2) 1-3 back to the AGC limiter 1-2, an absolute value circuit 1-4, a BEF circuit 1-5 that doubles the frequency of an input, for example, and a LPF circuit (fc, quality factor Q=0.7) 1-6 which filters the output of the BEF circuit 1-5. The control signal generation circuit 1b may be caused to function as a central frequency changing unit 1-1-1 for changing the setting of a central frequency between 5 and 15 Hz as desired. The BEF circuit 1-5 is a band elimination filter that eliminates specific frequencies and passes other bands.

The control signal generation circuit 1b may also include a memory 1-7 for storing the output of the second band-pass filter (BPF 2) 1-3.

Figure 1C:
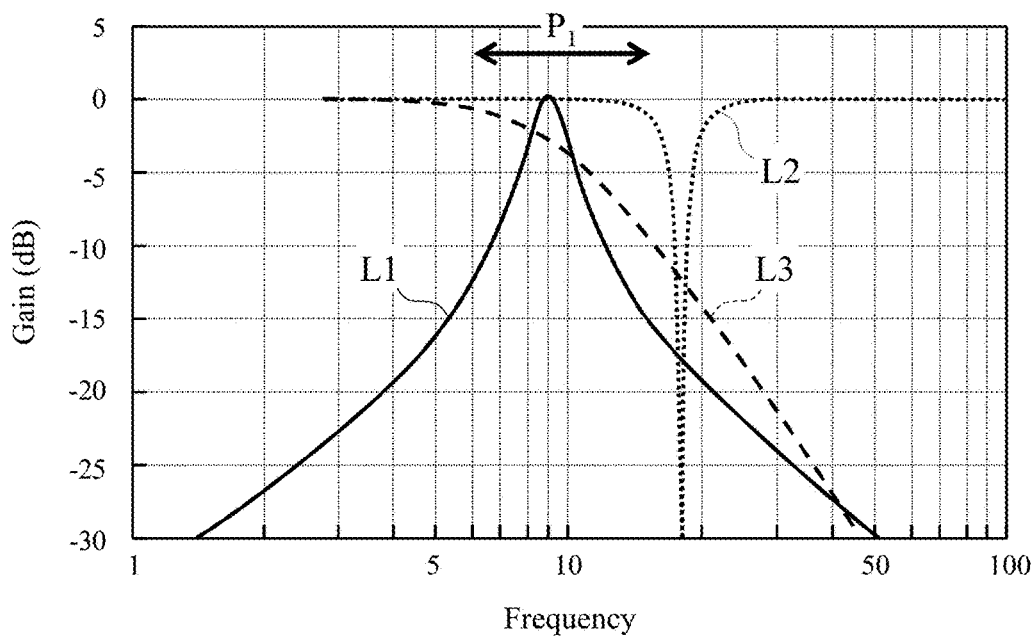
FIG. 1C is a diagram illustrating characteristics examples of a BPF, an AGC control notch, and a LPF.

FIG. 1C is a diagram illustrating examples of the frequency characteristic L1 of the BPF, an AGC control notch L2 of the AGC limiter 1-2, and the frequency characteristics L3 of the LPF 1-6. In the characteristics examples, the central frequency fc=9.0 Hz and Q=5.

The above characteristics make it possible for the control signal generation circuit 1b to output to the PWM modulation unit 3 a processed signal based on the brain waves in a frequency range indicated by sign P1.

FIG. 3B is a diagram illustrating an example of waveform processing by the circuit of FIG. 1B with reference to the relationship between frequency and amplitude.

A waveform 1) in (a) is an example of the waveform input to the first band-pass filter (BPF 1) 1-1. The vertical axis shows amplitude and the horizontal axis shows sampling time. The waveform 1) is a first waveform obtained by, for example, amplifying the brain waves of the individual (the subject brain waves).

A waveform 2) in (b) is an example of the waveform output from the first band-pass filter (BPF 1) 1-1. In the example, only the wavelengths of 7 to 13 Hz as illustrated in FIG. 2, for example, are extracted from the first waveform 1).

A waveform 3) in (c) is the waveform output from the AGC limiter 1-2 to which the waveform 2) has been input. In the waveform 3), amplitude variations depending on the individual are suppressed.

A waveform 4) in (d) indicates an example of the waveform output from the second band-pass filter (BPF 2) 1-3 to which the waveform 3) has been input. The BPF 2 (1-3) is provided as needed to perform a waveform shaping process.

In this way, it becomes possible to suppress individual differences while leaving differences in waveform among individuals, and to obtain a waveform that can be easily modified into a pulse signal.

The waveforms 3), 4) are waveform examples in a case in which a feedback function is implemented, as will be described below.

Figure 3C:
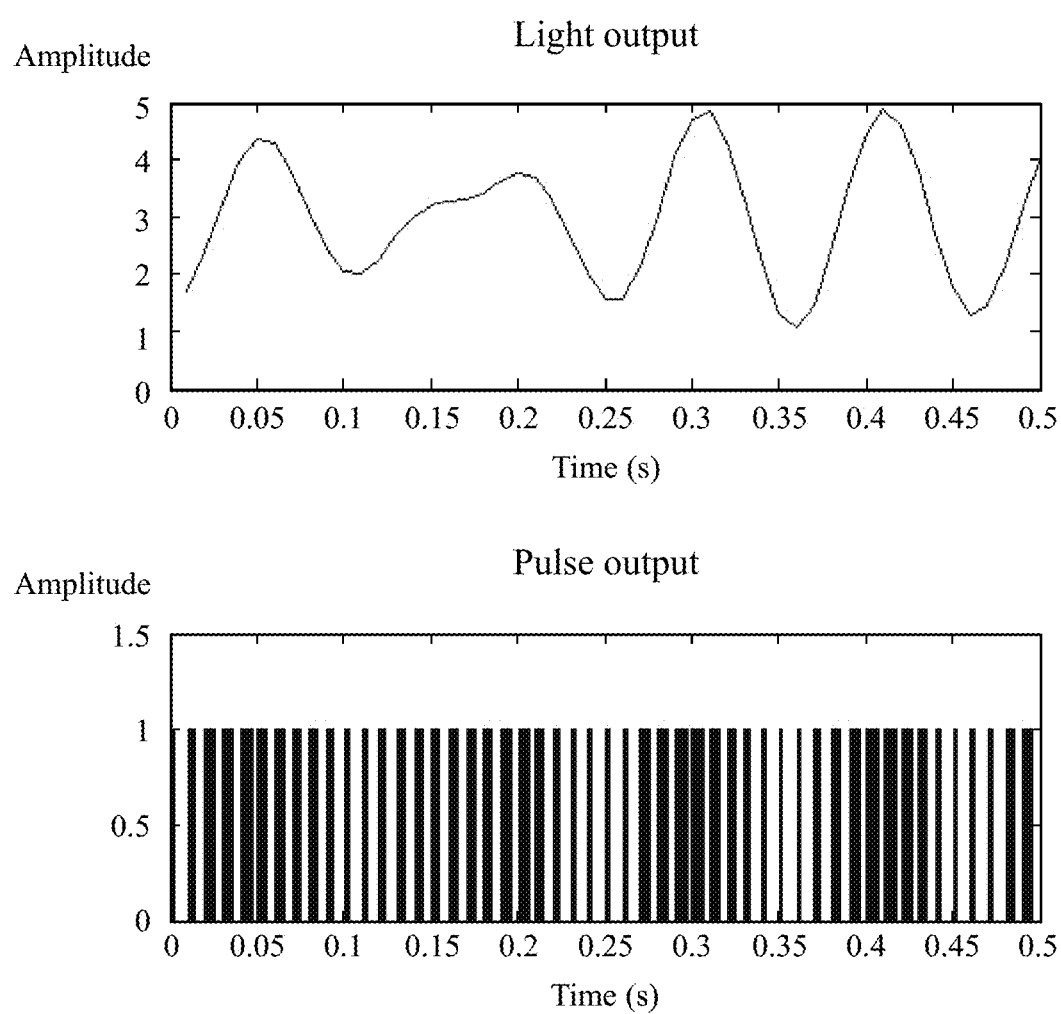
FIG. 3C illustrates an input waveform (a) and an output waveform (b) in a pulse modulation unit.

FIG. 3C illustrates input and output waveforms in the PWM circuit 3 to which the waveform 4) has been input. In FIG. 3C, the scale of the horizontal axis is modified. FIG. 3C(a) indicates the waveform 4) of FIG. 3B(d). In accordance with the period (frequency) and amplitude of the waveform 4), the duty of the pulse waveform is adjusted, as illustrated in FIG. 3C(b). Thus, it is possible to obtain in the PWM circuit 3 a pulse waveform in accordance with the waveform 4). Using the pulse waveform as a drive voltage for the LED 4, it becomes possible to suppress heat generation.

Figure 3D:
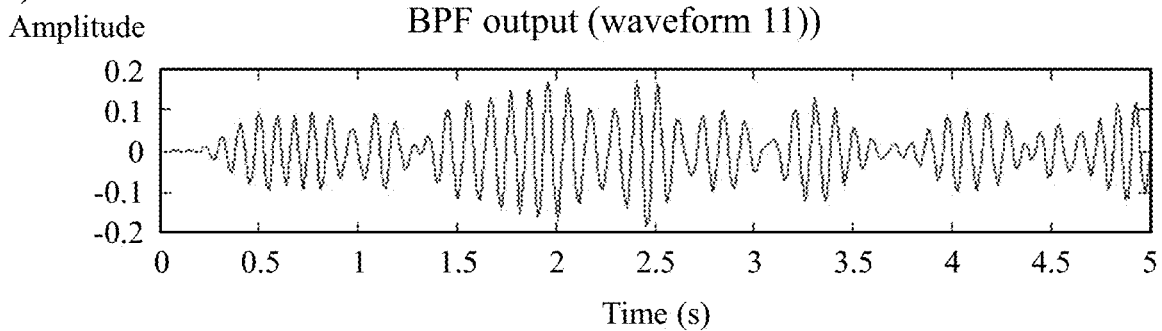
FIG. 3D illustrates an example of transition of waveform in a feedback circuit illustrated in FIG. 1B.
Figure 3D:
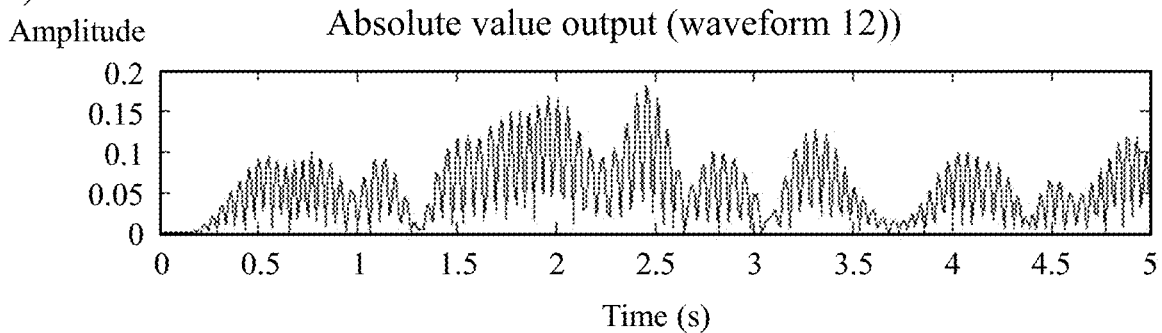
Figure 3D:
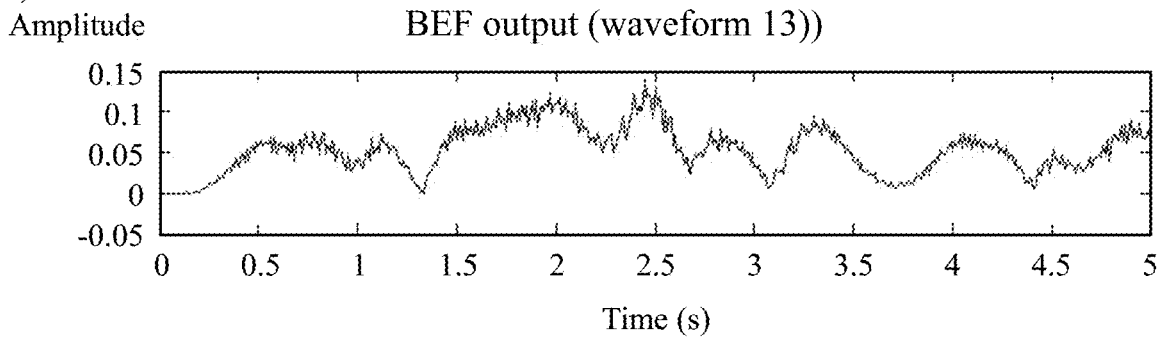
Figure 3D:
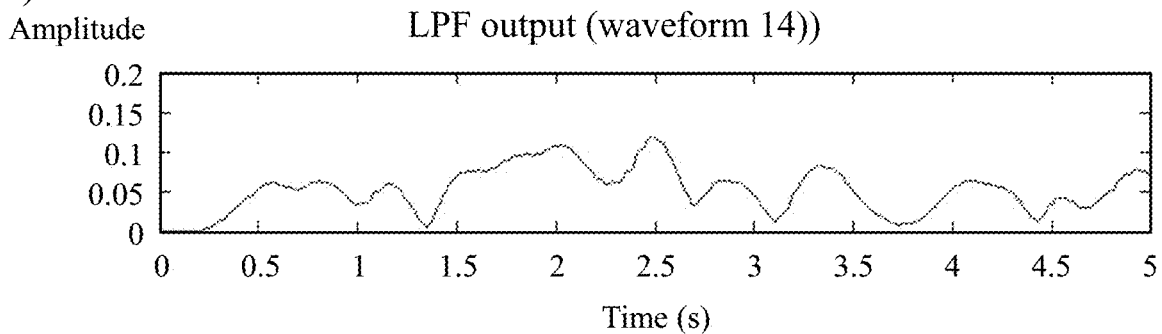

FIG. 3D illustrates an example of waveform processing by means of the feedback circuit in FIG. 1B.

A waveform 11) is an output waveform of the second band-pass filter (BPF 2) 1-3.

A waveform 12) is an example in which the waveform 11) is expressed in absolute values by the absolute value circuit 1-4. In this way, it becomes easier to compute the amplitude of the waveform.

A waveform 13) is an example in which the amplitude of the waveform 12) is suppressed by the BEF circuit 1-5 using the characteristics of the control notch illustrated in FIG. 1C.

A waveform 14) is an example in which, with respect to the waveform 13), the baseline amplitude is set to 0 and the amplitude is multiplied by a factor of 0.7 by the LPF 1-6.

By inputting the waveform 14) to a control terminal of the AGC limiter 1-2, it becomes possible to feed the amplitude depending on individual differences back to the AGC limiter circuit 1-2, and to suppress variations while maintaining individual characteristics.

Modifications

For example, the memory 1-7, in which the output of the second band-pass filter (BPF 2) 1-3 is stored, may store a waveform that is effective with respect to a particular individual, and subsequent pulse signals may be generated from the waveform from the memory. Alternatively, the brain waves may be stored in the memory. As a signal stored in the memory, any of the outputs of the circuit illustrated in FIG. 1B may be stored so as to simplify processing.

Third Embodiment

Figure 4:
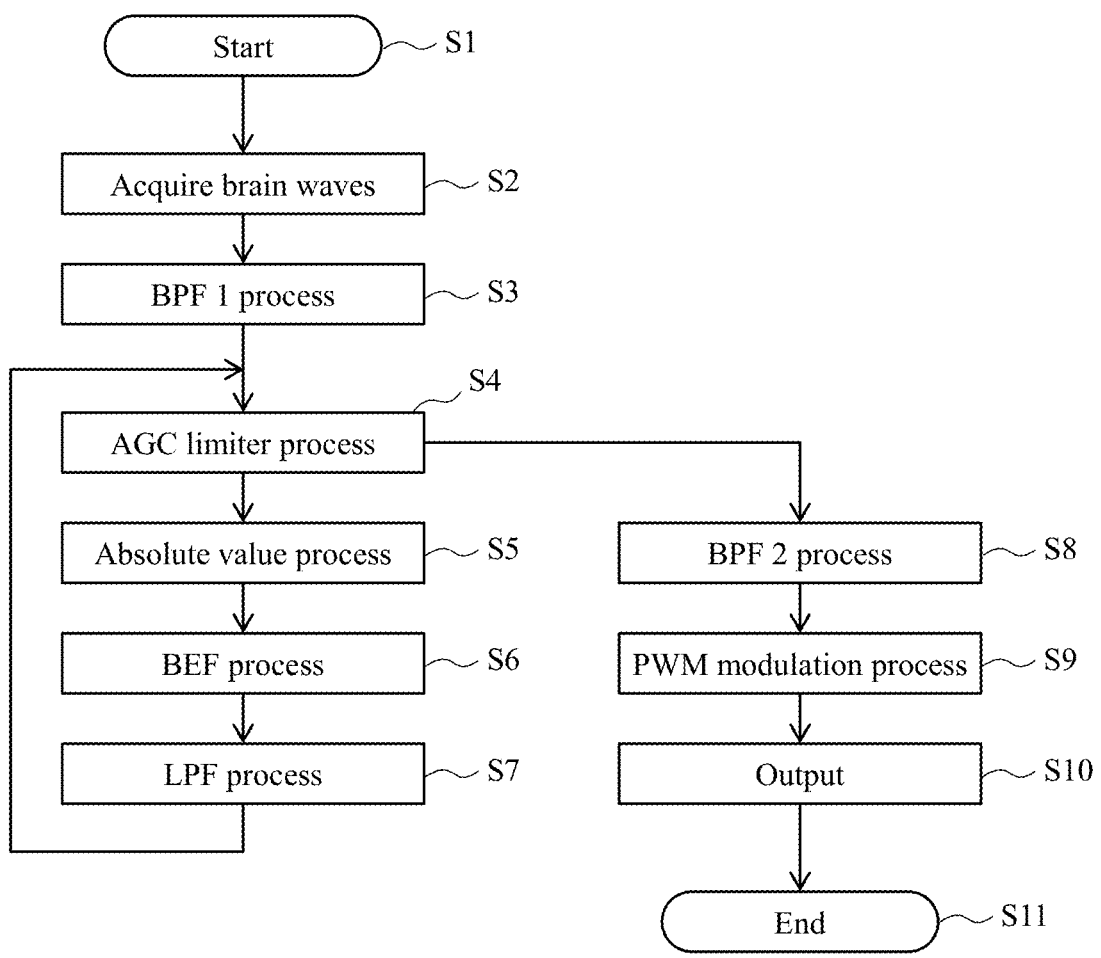
FIG. 4 is a flowchart illustrating an example of the flow of waveform processing.

FIG. 4 is a flowchart illustrating the flow of processing according to a third embodiment of the present invention, in which the processing performed in the first and second embodiments is implemented by software. As illustrated in FIG. 4, first, as the process is started (Start), brain waves are acquired in step S2. In step S3, the process of the BPF 1 is performed. In step S4, the process of the AGC limiter is performed. In step S5, the absolute value process is performed. In step S6, the BEF process is performed. In step S7, the process of the LPF is performed, and the results are returned to step S4. Then, in step S8, the process of the BPF 2 is performed. In step S9, the PWM modulation process is performed. In step S10, the drive pulse voltage is applied to the LED, and the process ends (step S11).

Fourth Embodiment

Figure 5:
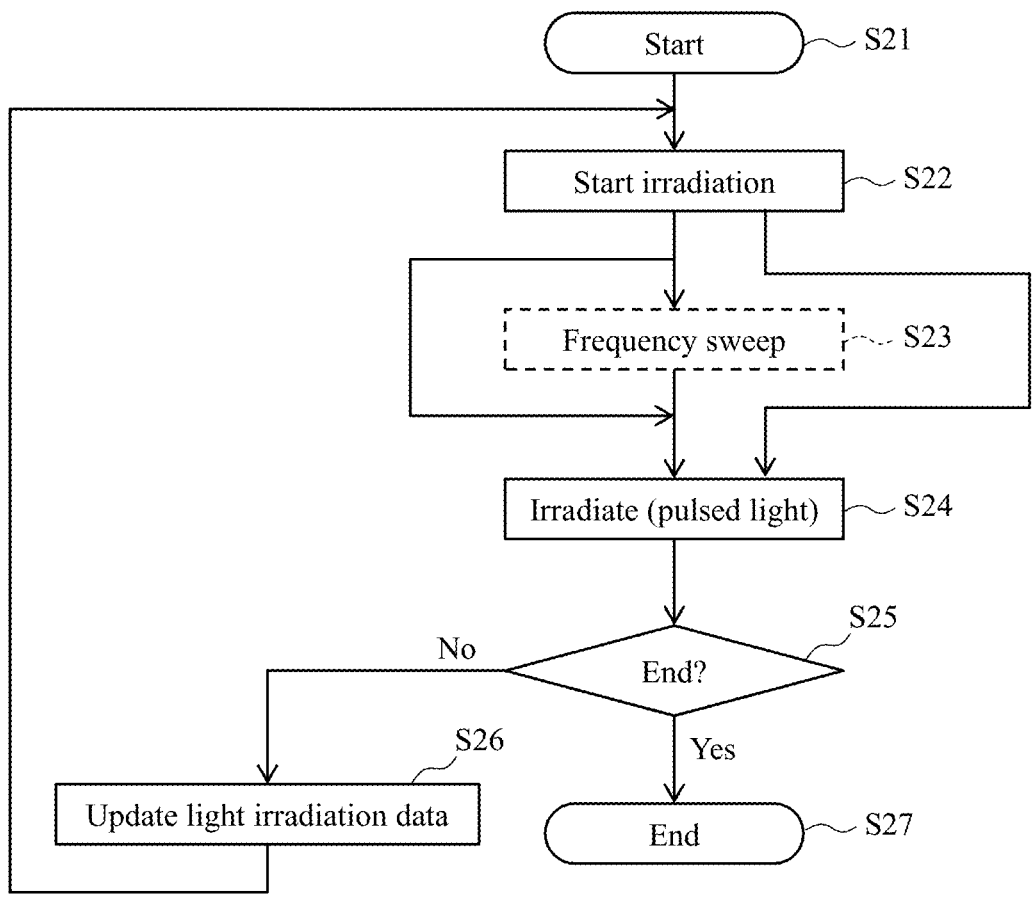
FIG. 5 is a flowchart illustrating the flow of a process of irradiating the head with light.

FIG. 5 is a flowchart illustrating the flow, according to a fourth embodiment of the present invention, of a process of irradiating the head of the subject with light using the LED which is driven on the basis of the LED drive pulse signal according to each of the first to third embodiments.

In step S21, a light pulse irradiation process is started (Start). In step S22, actual light irradiation is started. In step S23, a frequency sweep process may be performed for approximately three minutes. The frequency sweep process involves, for example, irradiation at frequencies from 13 Hz to 7 Hz at regular intervals of 0.1 Hz (approximately 3.5 seconds).

Then, in step S24, the head is irradiated with pulsed light. The irradiation is performed for approximately 12 minutes, for example. Until 12 minutes elapses according to a time counter and the like in step S25, the light irradiation data are updated in step S26, and the process returns to step S22. The process of updating the light irradiation data is a process such as illustrated in FIG. 4, i.e., a feedback process in which the results of processing of FIG. 4 based on the brain waves that have been changed by the light pulse irradiation is reflected in the LED drive pulse voltage. Preferably, the duration of irradiation is from 12 minutes (with a sweep) to 15 minutes (without a sweep), for example.

For example, based on the frequency region of the subject brain waves, the next updated data cause light pulse irradiation with respect only to a frequency region detected as the subject brain waves. Also with respect to amplitude, in accordance with the amplitude detected as the subject brain waves, the magnitude of amplitude is updated to become large if the detected amplitude is large and to become small if the detected amplitude is small. This feedback process makes it possible to eliminate the frequency sweep process.

Fifth Embodiment

The photic stimulation technology according to the present embodiment relates to an α-wave activation technology in which the head is irradiated with near-infrared LED light a waves (which may include θ waves as noted above) of the brain waves read from the subject, and feedback is performed.

Alpha (α) waves appear when awake and mentally relatively inactive. For example, α waves are generated when listening to music and relaxed. In a relaxed state, neuropeptides as an information transmitter are actively produced and natural killer cells are activated. Active natural killer cells help to prevent cancer or infectious diseases.

The near-infrared LED light passes through the cranium and reaches the brain surface. By performing feedback in synchronism with α waves, brain activation is promoted.

For example, in an Alzheimer-type dementia patient, symptoms such as a reduction of α waves, and slowing or loss of θ waves of low to intermediate amplitudes are observed.

If a light irradiation technology capable of activating the brain activity of such patient can be provided, it becomes possible to non-invasively reduce the symptoms without using drugs, and also to prevent cancer or infectious diseases.

With respect to the technology described with reference to the first to fourth embodiments, there have been cases in which, when the subject is subjected to the procedure, the effect cannot be obtained in the initial stage (early stage) before the subject becomes used to the device, and the subject may even feel ill.

Figure 6:
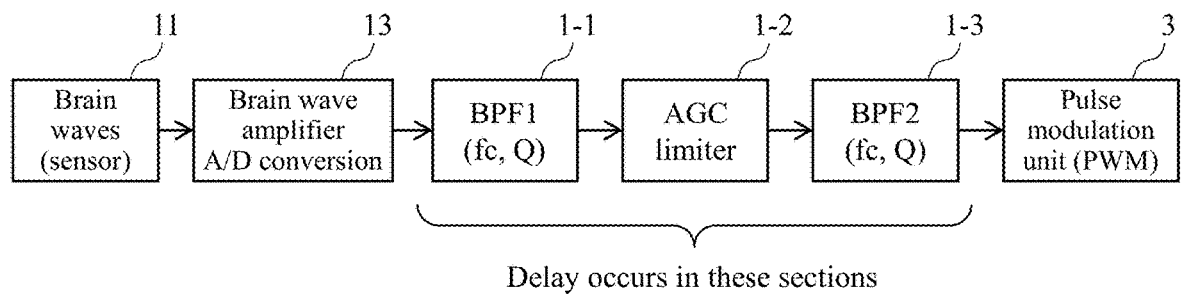
FIG. 6 is a functional block diagram illustrating a simple configuration example of a photic stimulation device according to the first embodiment.

The inventor presumed that this was because the brain waves of the subject and the phase of the feedback light of the device did not correspond to each other. FIG. 6 is a functional block diagram illustrating a simple configuration example of the photic stimulation device described with reference to each of the first to fourth embodiments, which is not equipped with the phase feedback function according to the present embodiment.

As illustrated in FIG. 6 (corresponding to FIG. 1B), in the photic stimulation device not equipped with the phase feedback function, a signal obtained from the brain waves is subjected to: A/D conversion in a microcomputer (brain wave amplifier, A/D conversion 13); a digital filtering process in the BPF 1 (1-1), the AGC limiter (1-2), the BPF 2 (1-3) and the like; and PWM modulation (3). The resultant control signal is output to the LED, which is not illustrated. Near-infrared light is fed back to the brain.

In this case, a signal delay is caused in the filter devices (1-1, 1-2, 1-3) and the like. The delay may possibly result in weakening the brain waves if the phase is displaced from the brain waves by 180 degrees, for example.

Accordingly, the inventor has conceived of a technology for approaching a positive feedback state by adjusting phase and frequency or delay.

In the following, the photic stimulation technology according to the embodiment of the present invention will be described with reference to the drawings. The technology achieves phase synchronization with the brain waves of the subject, and performs a feedback of near-infrared LED light.

Figure 7:
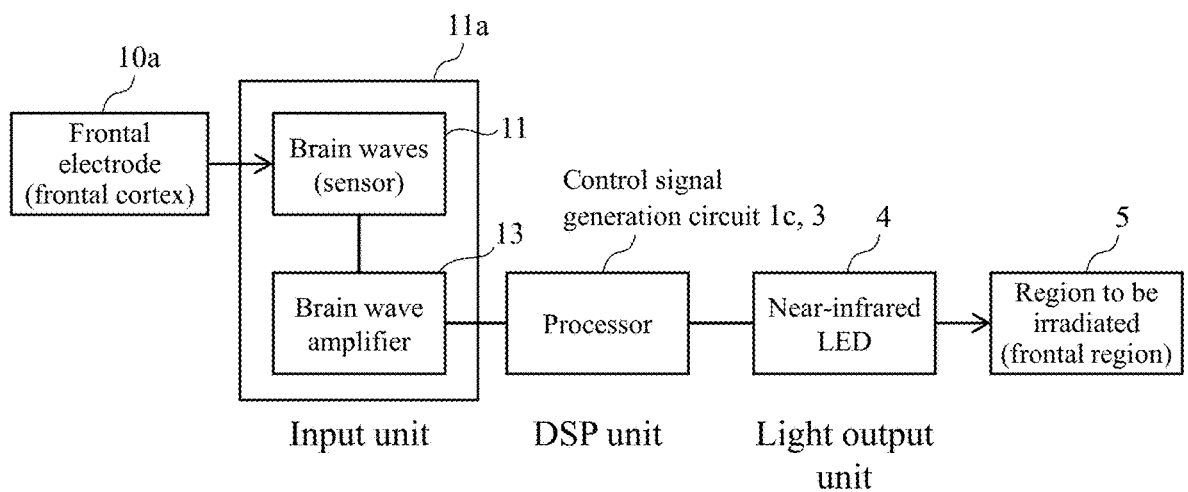
FIG. 7 is a functional block diagram illustrating a configuration example of a photic stimulation device according to a fifth embodiment of the present wave.
Figure 8:
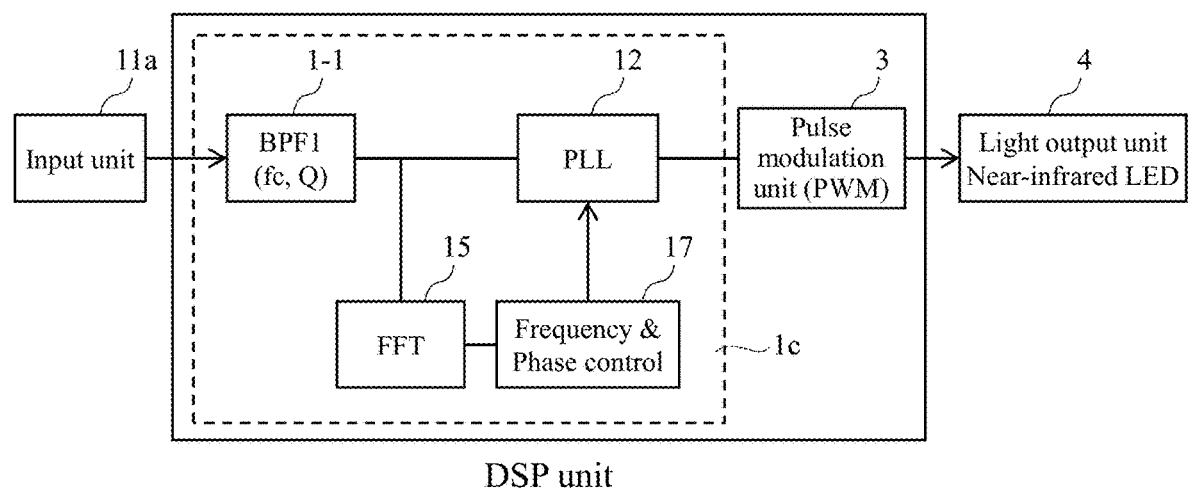
FIG. 8 is a diagram illustrating a configuration example of the signal processing device (DSP) of FIG. 7.
Figure 9:
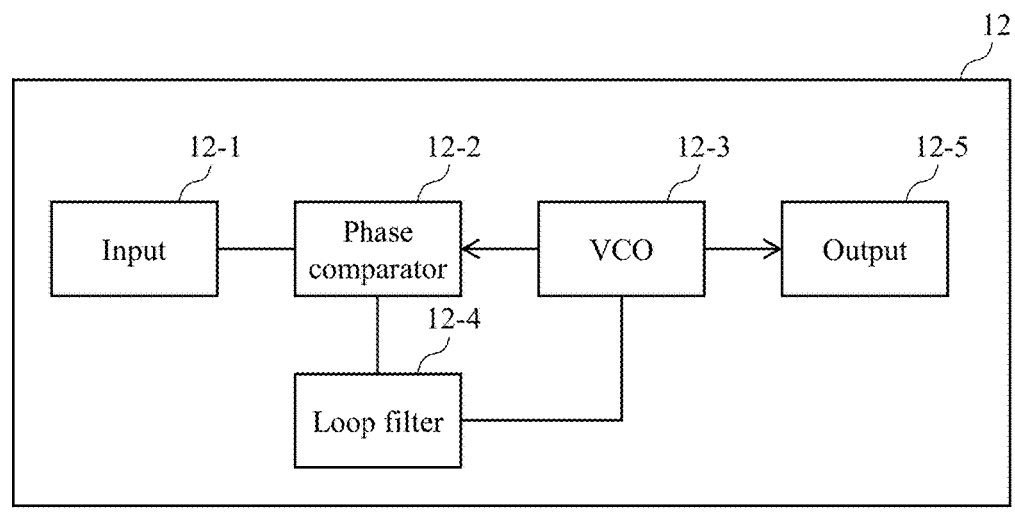
FIG. 9 is a functional block diagram illustrating a configuration example of the PLL of FIG. 8.

FIG. 7 is a functional block diagram illustrating a configuration example of the photic stimulation device according to the present embodiment. FIG. 8 is a diagram illustrating a configuration example of a signal processing device (DSP) of FIG. 7. FIG. 9 is a functional block diagram illustrating a configuration example of a PLL circuit of FIG. 8.

As illustrated in FIG. 7, the photic stimulation device according to the present embodiment includes a head electrode (attached to the frontal cortex) 10a, an input unit 11a, a DSP unit (signal processing unit, processor) 1c, 3, and a near-infrared LED 4. Near-infrared light from the LED 4 irradiates the region 5 to be irradiated of the frontal cortex.

A brain wave signal 11 is detected from the brain wave sensor 10a on the head (frontal cortex), and is amplified by an operational amplifier (brain wave amplifier) 13. The amplified brain wave signal is sampled by means of A/D conversion in a microcomputer, and read and processed by the DSP unit (processor) 1c, 3. The processed signal is output to the near-infrared LED (light output unit) 4 by PWM modulation.

As illustrated in FIG. 8, the DSP unit includes a BPF unit (1) 1-1, a phase-locked loop (PLL) unit 12, an FFT (Fourier transform) unit 15, and a control unit (frequency & phase control) 17 for frequency and phase control. The PLL unit 12 subjects the signal obtained from the BPF (1) 1-1 to FFT transform. Phase adjustment of the frequency or delay of the PLL 12 is performed so that the frequency level of target α waves becomes high.

The data that have been read from the brain wave sensor 11 on the head and subjected to A/D conversion are limited by the BPF (1) 1-1 in a range of 1 to 30 Hz, for example, including the wavelength band of α waves. For example, FFT data are acquired 70 times per 10 seconds, and a moving average of the data is calculated (the details of the process will be described below).

Thereafter, a maximum value in the α waves is detected, and the PLL 12 is locked at the frequency of the α waves for the next 10 seconds, for example. At the time of switching, the PLL 12 can be synchronized with the sampled brain wave data. The signal of the maximum value of the α waves output from the PLL 12 is subjected to PWM modulation (3) and causes the near-infrared LED 4 to emit light.

As illustrated in FIG. 9, the PLL 12 includes an input unit 12-1, a phase comparator 12-2, a VCO 12-3, a loop filter 12-4, and an output unit 12-5.

When the input signal is φ[n]=x_{re}[n]+jx_{im}[n], the phase is as follows.

$$\Phi[n] = \tan^{-1}\left(\frac{x_{im}[n]}{x_{re}[n]}\right)$$

In the phase comparator 12-2, the phase φ[n] of the input signal and the phase ψ[n] of the VCO 12-3 returning from feedback are compared.

$$u[n]=\phi[n]-\psi[n]$$

The output u[n] of the phase comparator is input to the loop filter 12-4. The transfer function of the loop filter 12-4 is expressed by the following equation.

$$H[n] = g_1 + \frac{g_2}{1 - z^{-1}}$$

When the input signal of the loop filter 12-4 is u[n] and the output signal thereof is θ[n], the corresponding difference equations are as follows.

$$v[n]=v[n-1]+g_2 u[n]$$

$$\theta[n]=g_1 u[n]+v[n]$$

The output θ[n] of the loop filter 12-4 represents a phase difference. The VCO 12-3 is controlled so as to fill the phase difference, and feeds back a phase output ψ[n] to the phase comparator 12-2.

The output of the phase comparator 12-2 is as follows.
φ[n]−ψ[n], the range is [−2π, 2π]rad
This is corrected to be as follows.
[−π, π]rad
Then, the transfer function H(z) of the loop filter 12-4 is expressed by the following.

$$H(z) = g_1 + \frac{g_2}{1 - z^{-1}}$$

The VCO 12-3 is a delay-free loop.

Figure 10:
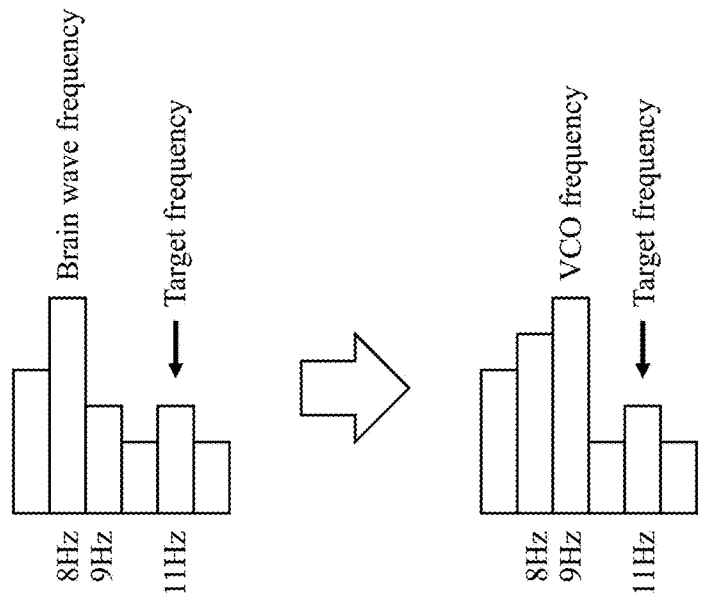
FIG. 10 is a diagram illustrating an example of a control algorithm according to the present embodiment.

FIG. 10 is a diagram illustrating an example of a control algorithm according to the present embodiment.

This method is a method whereby the maximum value is discovered from the signals that have been subjected to FFT analysis, and the frequency is controlled so as to be guided to a target frequency.

A spectrum measured from the brain waves is searched for a maxima in the vicinity of α waves, and initially, the PLL frequency at the maximum is fed back to the LED.

Assuming that the target frequency is higher than the frequency of the maximum, in the next control procedure, a frequency greater than the maximum by 1 Hz is set, for example. Then, because the frequency is higher by 1 Hz, the phase rotates faster by one wavelength in one second.

As a result, the frequency approaches the target frequency due to the feedback. As the level of the maximum+1 Hz increases, the frequency is brought closer to the target frequency again by 1 Hz at a time. Upon reaching the target frequency, the frequency is maintained.

The conditions for the computation are as follows.

BPF 1: Sampling frequency 258 Hz, central frequency fc 10 Hz, pass-band width 5 to 15 Hz FFT: Sampling frequency 128 Hz, analysis rate twice per sec, analysis resolution 0.5 Hz For the frequency switching, an average at 10 second intervals of the results of FFT is used, for example.

PLL: The output level is determined by the VCO setting.

DELAY is adjusted from 0 to 0.2 s to (in the case of 5 Hz) by the α-wave frequency.

The method of sampling and the moving average (arithmetic mean) processing of FFT will be described.

The processing is performed under the following conditions.

Frequency band of brain waves: 0.13 to 128 Hz
Frequency band of α waves: 7 to 14 Hz
Sampling frequency: 128 Hz×2=256 Hz
Required sampling time: 1/7 Hz=0.143 s
Time for averaging: 10 s
The number of times of averaging: 10×2/0.143≈140
The sampling method is as follows.

The sampling frequency is twice according to the Nyquist frequency theorem. Since the lowest frequency of α waves is 7 Hz, the necessary sampling time is 0.143 s. Increasing the sampling time makes it possible to extend the frequency band to δ waves. However, this will result in a decrease in the number of times of averaging. Accordingly, FFT for use in feedback and FFT for use in analysis may be divided.

FFT Averaging

FFT averaging will be described.

Figure 11:
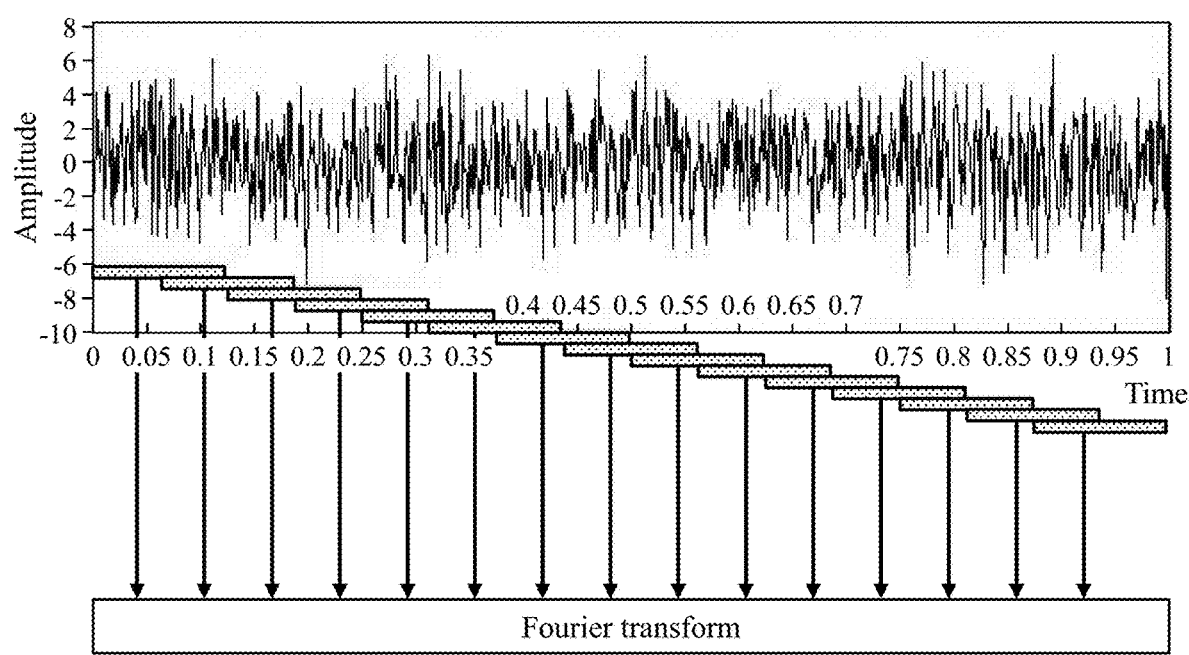
FIG. 11 is a diagram illustrating an example of a method of determining an average of FFT.

FIG. 11 is a diagram illustrating an example of a method of determining an average. The vertical axis shows amplitude and the horizontal axis shows time, wherein the unit is arbitrary; in practice, the unit is on the order of microseconds.

The brain waves are sampled by A/D conversion, and an FFT analysis is performed. For example, FFT data are averaged for the duration of 10 seconds (0.1 in the figure), and the maximum frequency in the α-wave frequency band is detected. The frequency is reflected in the frequency of the VCO for the next 10 seconds.

The method of averaging includes performing a Fourier transform a plurality of times, as illustrated in FIG. 11.

Because the sampling time is 0.143 s, it is possible to acquire FFT data for 70 times. However, since FFT is processed using a window function, it is preferable to take the average by overlapping halves of the sampling time.

Accordingly, for example, data for 140 times of FFT are averaged. By averaging, white noise decreases according to 1/√N, where N is the number of times of averaging.

Figure 12:
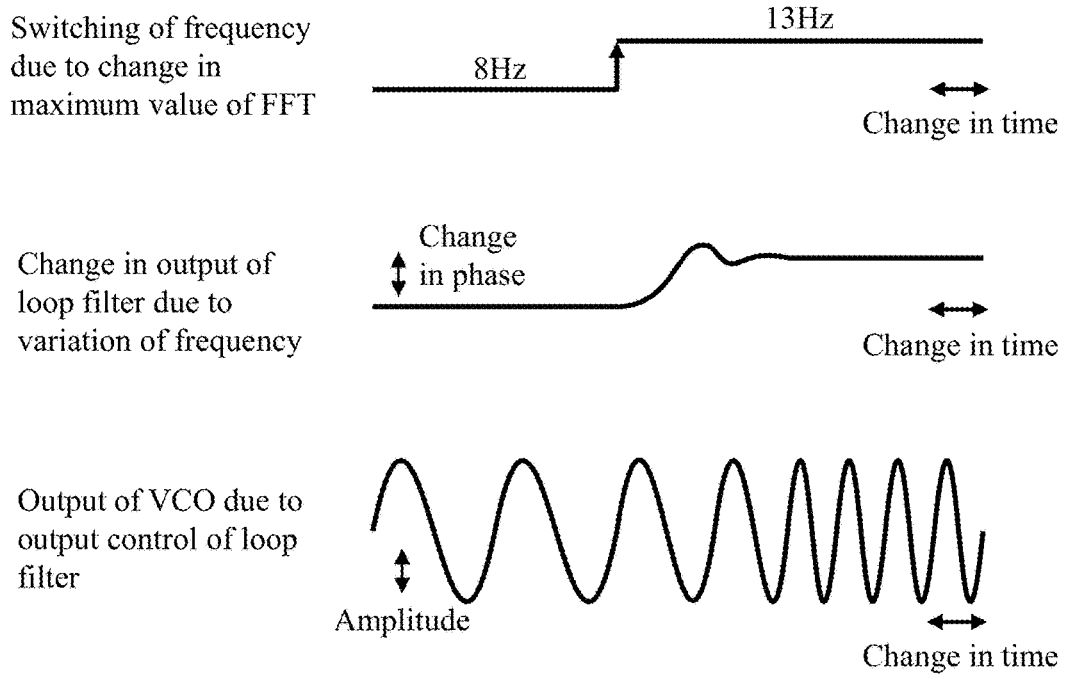
FIG. 12 is a diagram illustrating a displacement in the maximum frequency of α waves and the behavior of a VCO.

With reference to FIG. 12, displacement of the maximum frequency of α waves and the behavior of the VCO will be described.

FFT data extracted from the brain waves are averaged to detect the maximum frequency of α waves. If the maximum frequency of α waves has varied, the VCO frequency is changed in the next 10 seconds. However, the frequency of the VCO is not changed sharply (FIG. 12 (top of FIG. 12), but is stably varied (bottom of FIG. 12) to a target frequency by means of the loop filter (middle of FIG. 12). The phase is gradually displaced and connected to the target frequency.

FIG. 12 illustrates an analog IC PLL process. In digital signal processing, the phase difference is represented by numerical values.

The amplitude is determined by the VCO. The value of the amplitude can be set by means of a program. Accordingly, it is possible to decrease the signal level for an initial operation, or to change the signal level in proportion to the level of the maximum frequency of the FFT.

Figure 13:
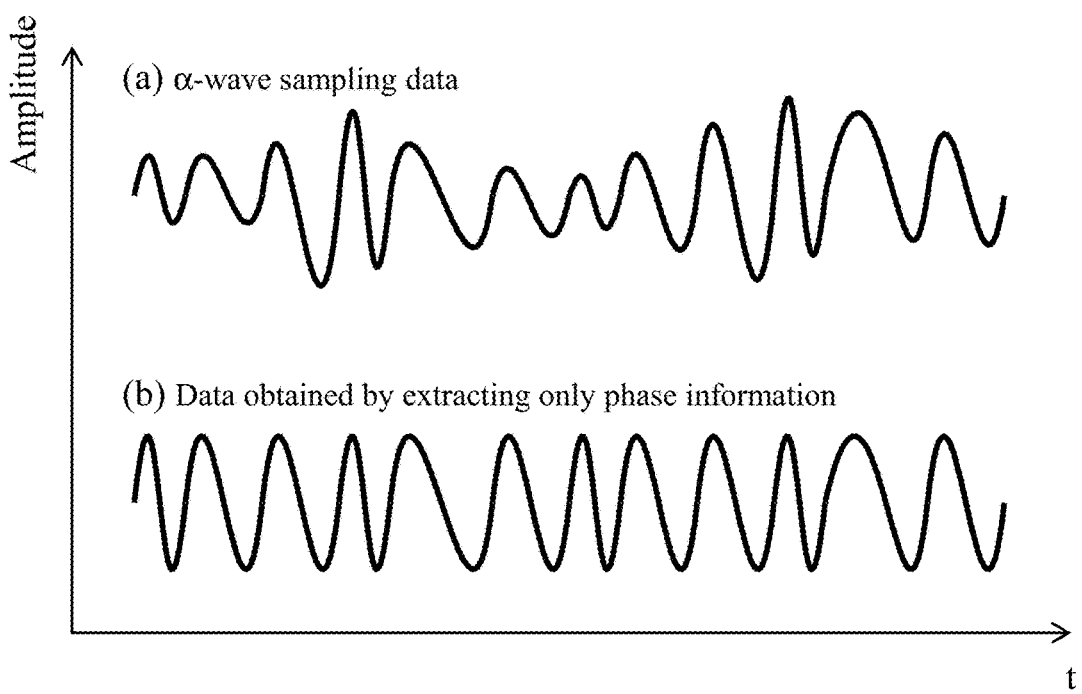
FIG. 13 is a diagram illustrating a phase synchronization method.

FIG. 13 is a diagram illustrating a phase synchronization method. The horizontal axis shows time and the vertical axis shows amplitude. In FIG. 13, the upper waveform represents sampling data of α waves, and the lower waveform represents data obtained by extracting only phase information.

The BPF switches frequencies at 10-second intervals. At the time of switching, phase alignment with the input brain waves is performed. That is, only the phase data are extracted from the α-wave sampling data, and the amplitude is made constant. From the sampling data obtained by only extracting the phase at the time of frequency switching at the 10-second intervals, the phase is computed according to:

θ=tan$^{-1}$(A/B).

The phase is aligned with the phase of the VCO.

The method of phase synchronization at the time of frequency switching will be described. The best one from the test results can be selected.

1) Synchronization Method 1

Figure 14:
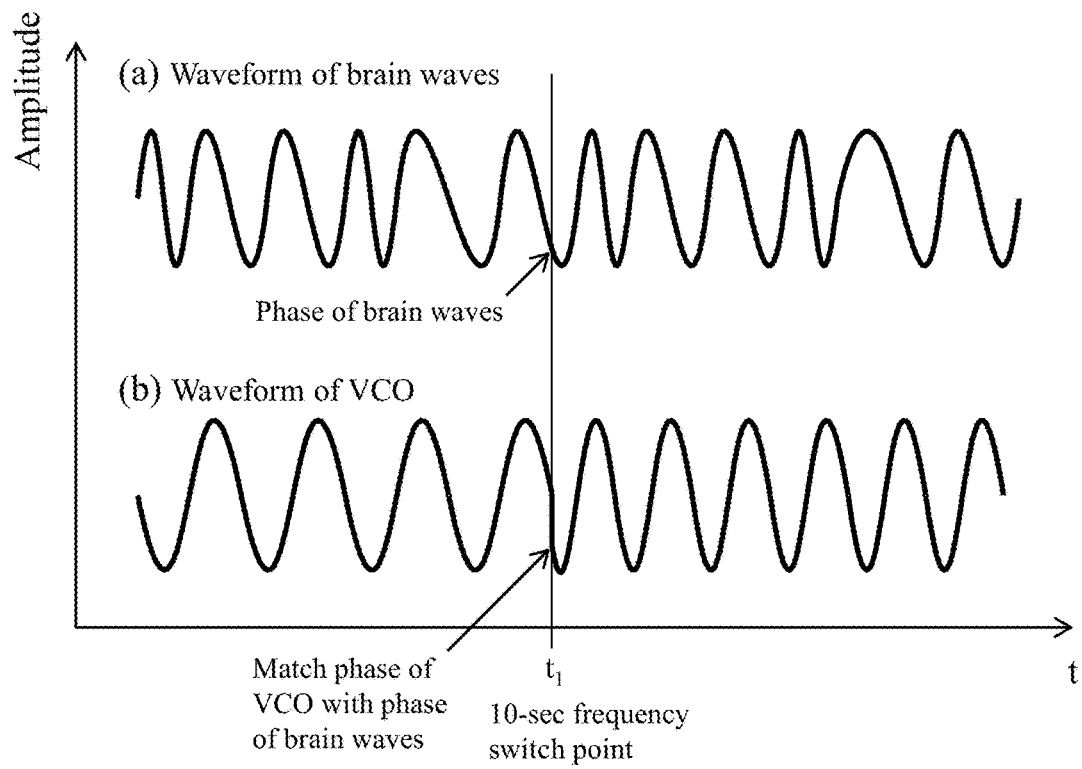
FIG. 14 illustrates a first synchronization method in which the horizontal axis shows time and the vertical axis shows amplitude.

FIG. 14 illustrates a first synchronization method, where the horizontal axis shows time and the vertical axis shows amplitude. The first synchronization method is a method of achieving phase synchronization at the time of frequency switching. For example, the frequency of the VCO for the next 10 seconds is determined using the data of an average of 10 seconds of FFT processing. Using the phase computed by this method, the operation of the VCO is started.

FIG. 14 shows a graph indicating the switching of the frequency of the VCO from a low frequency to a high frequency. At the time of switching, the phase of the sampling data (phase of brain waves) and the phase of the start of the VCO can be aligned.

It should be noted, however, that the phase of the VCO before switching and the phase of the VCO after switching are not matched. Thus, the possibility of a DC variation remains.

2) Synchronization Method 2

FIG. 15 to FIG. 18 illustrate a second synchronization method, where the horizontal axis shows time and the vertical axis shows amplitude. The second synchronization method is a method of achieving phase synchronization at a zero-crossing point after a frequency switch. For example, a delay is provided until the zero-crossing point of the brain waves is reached after a 10-second frequency switching point, and then synchronization is achieved.

Due to the synchronization of the phase of brain waves and the phase of the VCO, a blank time is generated before the zero-crossing point. While no unwanted harmonics are generated, if the phase of brain waves does not return to zero soon enough, the blank period may become longer.

Figure 15:
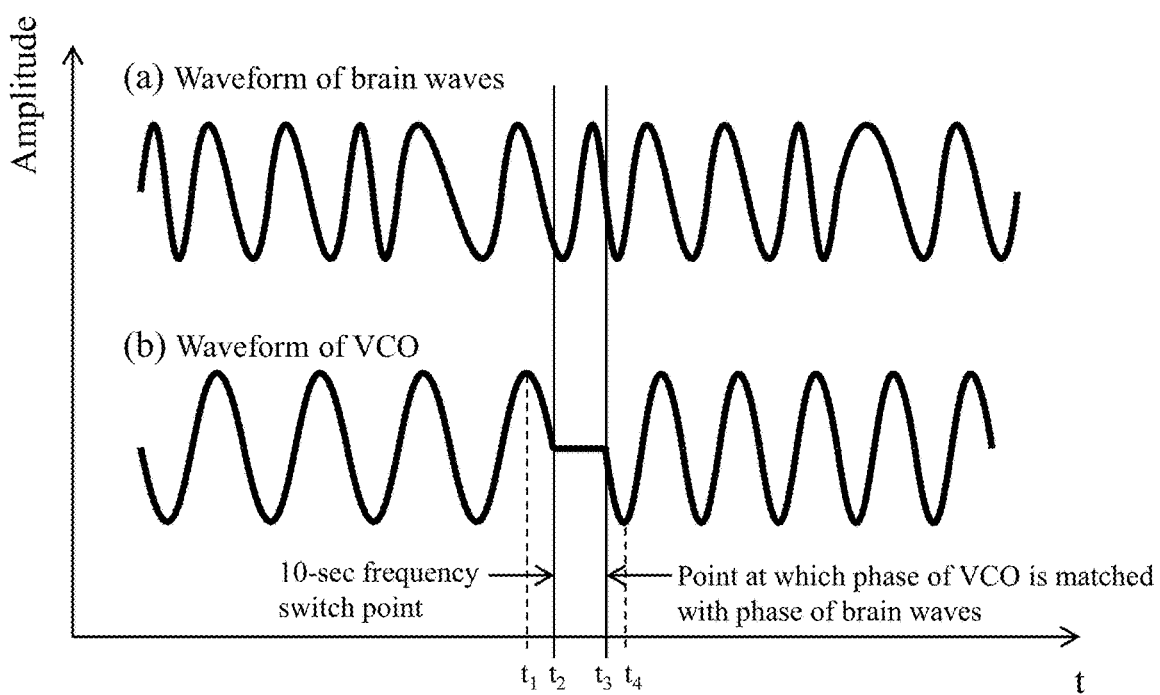
FIG. 15 is a diagram illustrating a first example of a second synchronization method.
Figure 16:
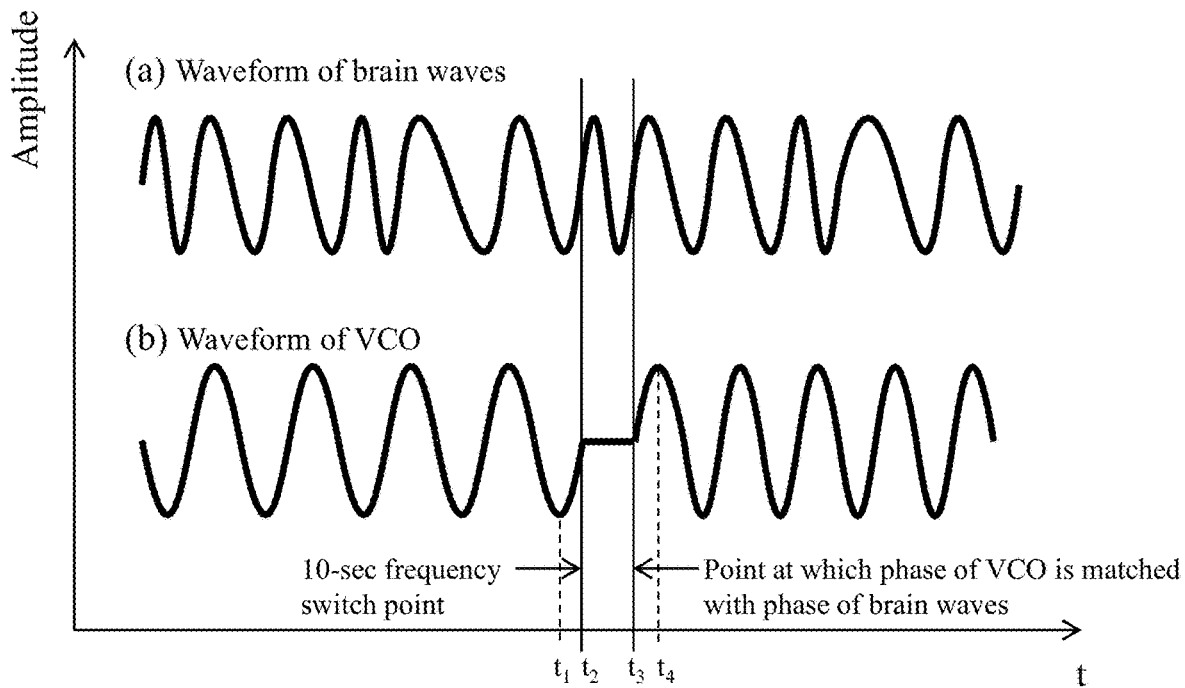
FIG. 16 is a diagram illustrating a second example of the second synchronization method.

Referring to FIG. 15 and FIG. 16, the upper waveform is that of the brain waves, and the lower waveform is that of the VCO. Between the 10-second frequency switching point $t_2$ and a point $t_3$ at which the phase of the VCO is matched with the phase of brain waves, the waveform of the VCO is maintained at zero. FIG. 15 illustrates an example in which zero-crossing occurs in a period in which the amplitude of the waveform of the VCO decreases from $t_1$ to t2 ($t_1<t_2$). FIG. 16 illustrates an example in which zero-crossing occurs in a period in which the amplitude of the waveform of the VCO increases from $t_1$ to $t_2$ ($t_1<t_2$). After the 10-second frequency switching point, a delay is provided until a zero-crossing point of the brain waves is reached, and then synchronization is achieved.

Figure 17:
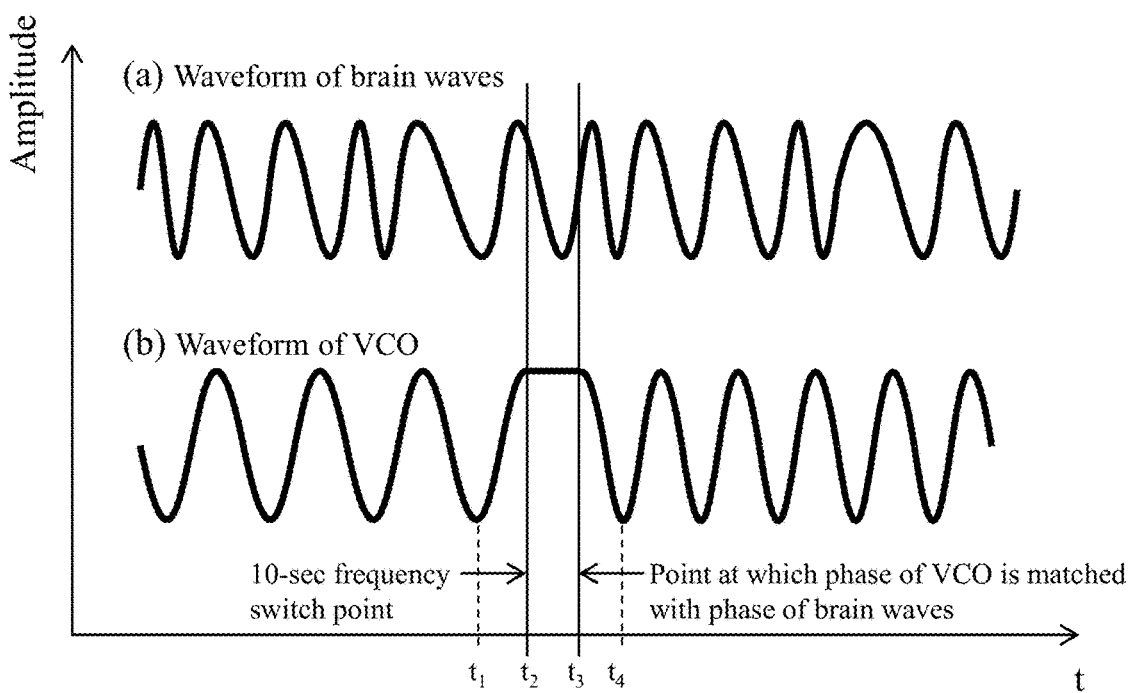
FIG. 17 is a diagram illustrating a third example of the second synchronization method.
Figure 18:
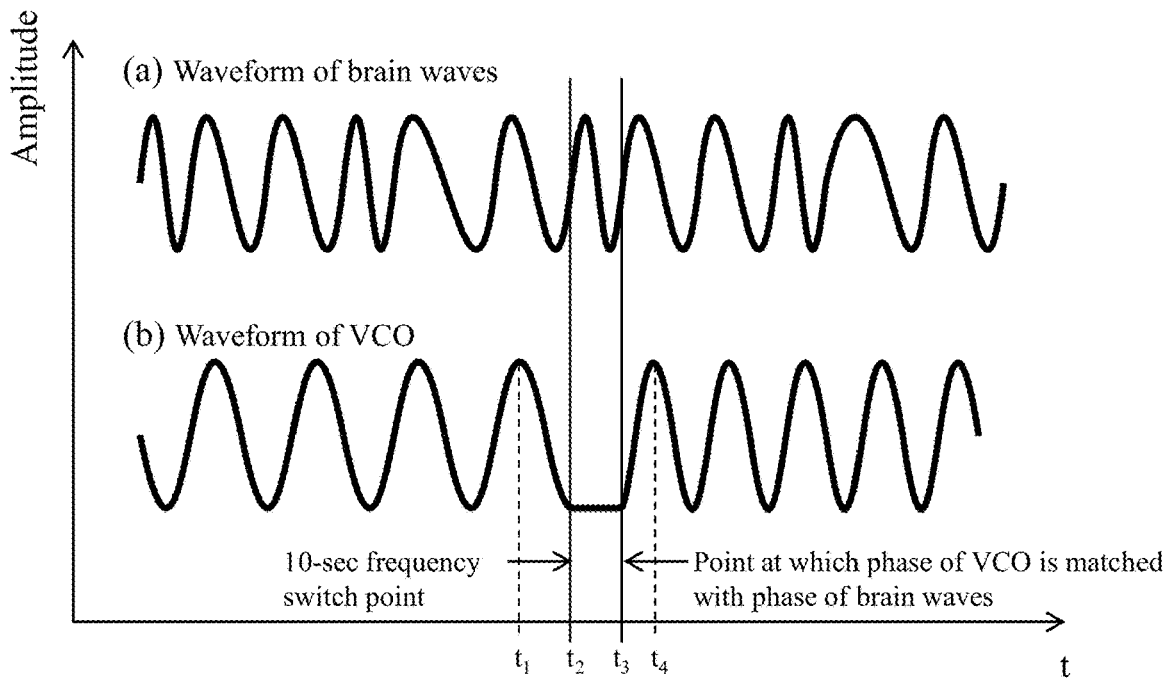
FIG. 18 is a diagram illustrating a fourth example of the second synchronization method.

FIG. 17 illustrates an example in which the timing at which the maximum in the waveform of the VCO is obtained is at the 10-second frequency switching point. FIG. 18 illustrates an example in which the timing at which the minimum in the waveform of the VCO is obtained is at the 10-second frequency switching point.

Because the phase of brain waves and the phase of the VCO are synchronized by either of the above synchronization methods, a blank time is produced before the zero-crossing point. While no unwanted harmonics are generated, if the phase of brain waves does not return to zero soon enough, the blank period may become longer.

Figure 19:
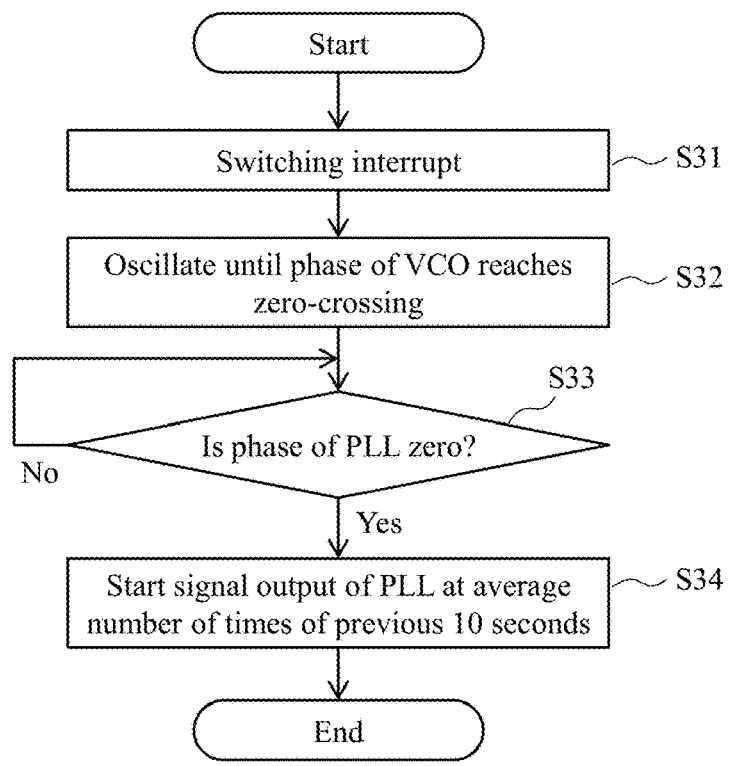
FIG. 19 is a flowchart illustrating an example of the flow of the second synchronization process.

FIG. 19 is a flowchart illustrating an example of the flow of the above synchronization process. As illustrated in FIG. 19, the process is started (Start), and then a switching interrupt (pause) is performed at timing $t_1$ (step S31).

Then, in step S32, oscillation is continued until the phase of the VCO comes to the zero-crossing point.

In step S33, it is determined whether the phase of the PLL is zero. If zero (Yes), the process advances to step S34. If No, the process waits until the phase of the PLL becomes zero.

In step S34, signal output of the PLL is started at the average frequency of the previous 10 seconds, and the process ends.

In this way, it becomes possible to synchronize the phase of the control signal to the near-infrared LED with the phase of the subject brain waves.

In the present embodiment, when the subject is subjected to the procedure, the brain waves of the subject and the phase of the feedback light of the device are aligned. This provides the advantage that the effect of the technology according to the first to fourth embodiment can be obtained even in the initial stage (early stage) before the subject becomes used to the device.

Sixth Embodiment

Figure 20:
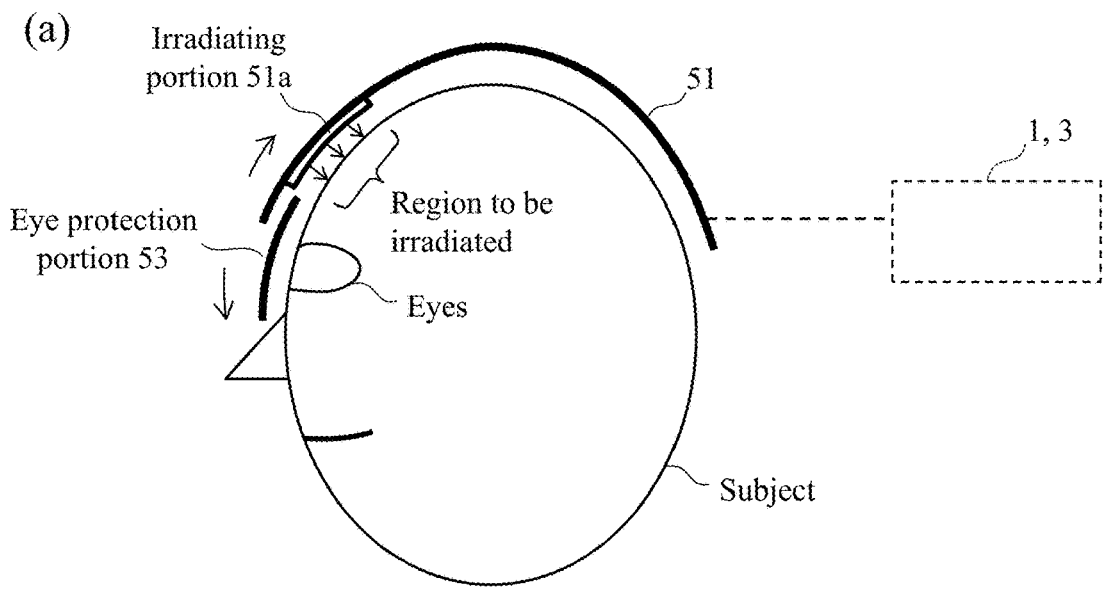
FIG. 20 is a diagram illustrating a configuration example of a light irradiation device according to an embodiment of the present invention.
Figure 20:
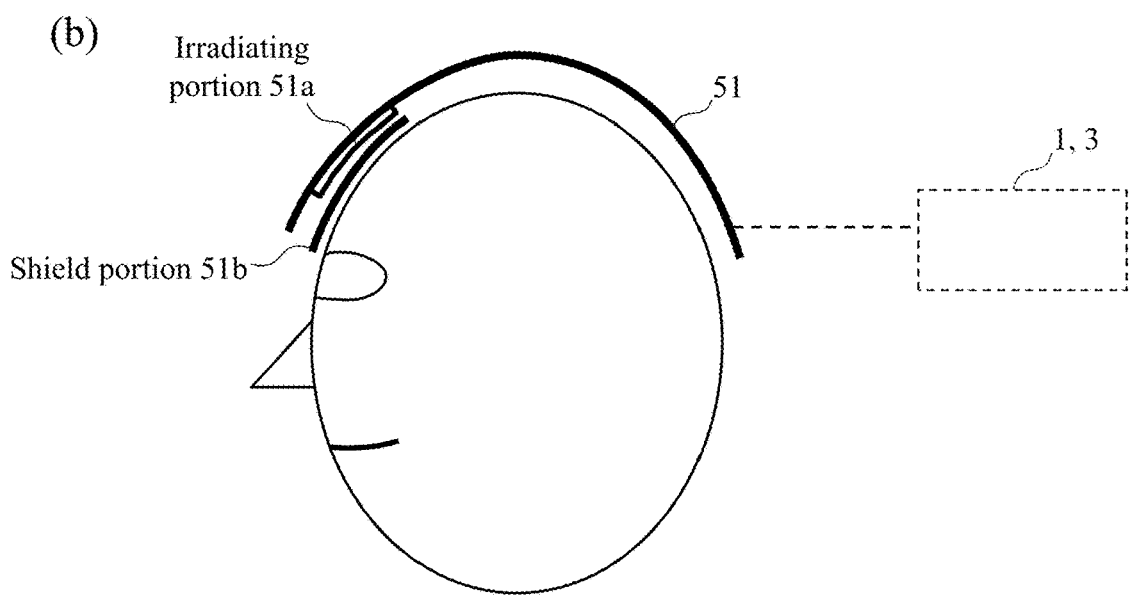
Figure 20:
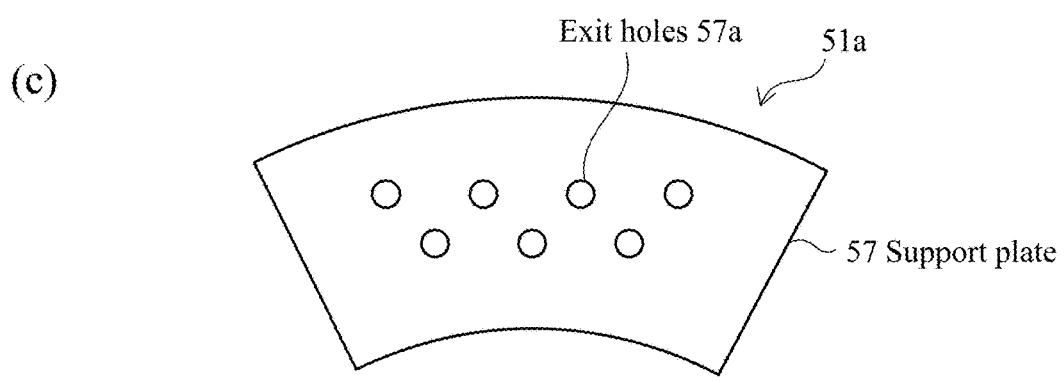

FIG. 20 is a diagram illustrating a configuration example of the photic stimulation device according to a sixth embodiment of the present invention, illustrating an example of an instrument for irradiating the head of the subject with red pulsed light obtained by performing the process according to each of the first to sixth embodiments. As illustrated in FIG. 20(c), a support plate 57 has exit holes 57a in which a number of LEDs 4, not illustrated, are arranged. The subject wears a cap-like member 51 which is fitted with the support plate 57 on a back surface (in the region to be irradiated of the head) thereof.

On the basis of the pulse drive voltage generated by the waveform generation unit 1a, the pulse modulation unit 3 (FIG. 1A) and the like, the head is irradiated with the red light. At this time, the position of an irradiating portion 51a of the cap-like member 51 is matched with the region to be irradiated. Then, when light irradiation actually takes place, an eye protection portion 53 slidably attached to the cap-like member 51 is slid to the position of the eyes to protect the eyes (FIG. 20(a)).

As illustrated in FIG. 20(b), the eye protection portion 53 can be slid out of the position of the eyes and positioned between the irradiating portion 51a and the region to be irradiated. In this way, the light from the irradiating portion 51a can be blocked and the eyes can be protected.

As described above, according to the present embodiment, light irradiation and protection of the eyes can be effectively achieved.

Seventh Embodiment

Figure 21:
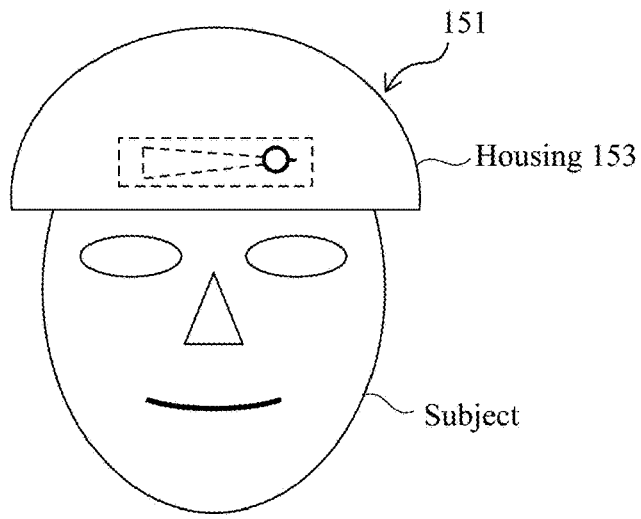
FIG. 21 is a diagram illustrating a configuration example of a photic stimulation device according to a seventh embodiment of the present invention, illustrating another example of an instrument for irradiating the head of a subject with a red-ray pulsed light obtained by performing a process according to each of the first to sixth embodiments.
Figure 21:
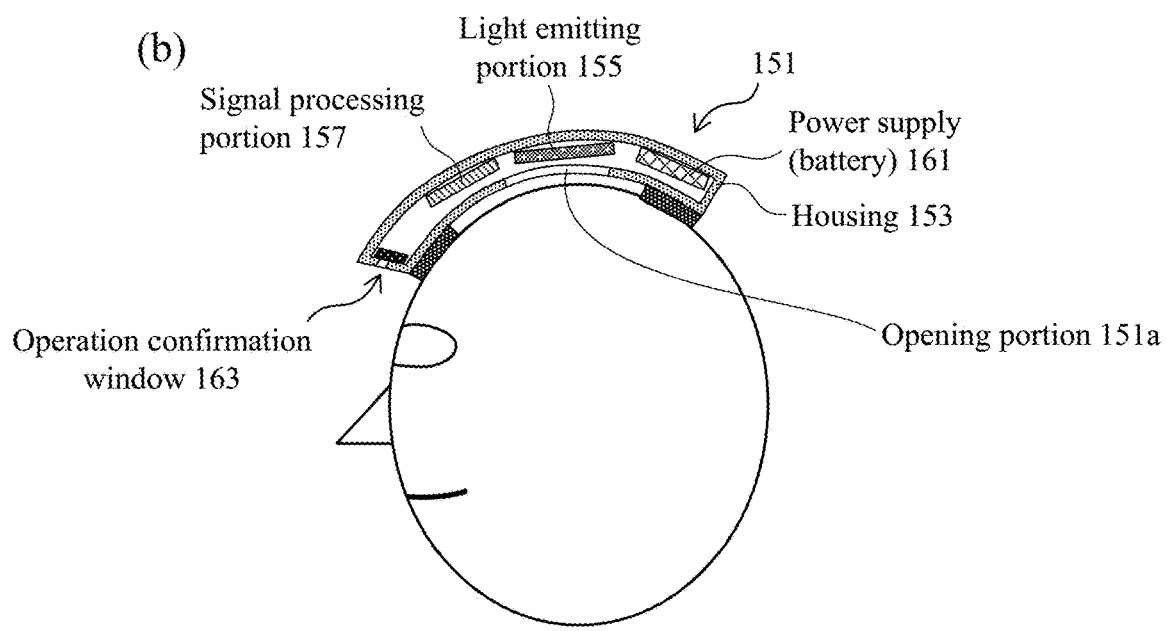
Figure 21:
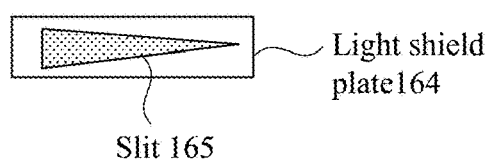
Figure 21:
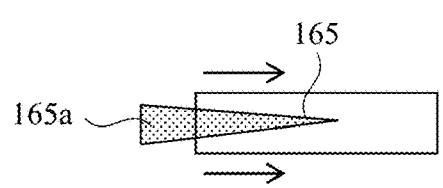

FIG. 21 is a diagram illustrating a configuration example of the photic stimulation device according to a seventh embodiment of the present invention, illustrating another example of an instrument for irradiating the head of the subject with red-ray pulsed light obtained by performing the process according to each of the first to sixth embodiments.

Referring to FIG. 21(a), (b), a light pulse device 151 worn on the head includes a device housing 153 in which, in addition to a light emitting portion 155, a signal processing unit 157 and a power supply (such as a battery) 161 are arranged, for example. The signal processing unit 157 and the power supply (such as a battery) 161 may be arranged outside the housing 153.

In order to easily monitor the operation (starting and stopping) of the light for stimulating the brain, the configuration, as illustrated in FIG. 21(b), (c), includes a function for guiding some of the light in the housing 153 to a location visible to the user's eyes, and projecting operation monitoring light onto the user.

Thus, the light pulse device 151 to be worn on the head includes, in a position visible to the eyes, a window 163 which makes it possible to confirm part of the internal photic stimulation signal for confirming the operation of the apparatus. On a light guide path for the light in the direction of the eyes, an adjustment window for dimming is provided. When it is desired to change brightness, the adjustment window can be operated to adjust the brightness.

The adjustment of light by means of the adjustment window 163 may use colorants having different values of transmittance, a shield on the light guide path, or any other device with which the brightness of the confirmation light can be adjusted in the operation confirmation window.

For example, as illustrated in FIG. 21(c), (d), the function may include the operation confirmation window 163 provided with an adjusting switch function for dimming or shielding the operation monitoring light.

The adjusting switch function includes, for example as illustrated in FIG. 21(c), (d), a slit 165 and a light-shield plate 164 configured to adjust the opening range of the slit 165, in a position facing the operation confirmation window 163. By sliding the light-shield plate 164, the opening range of the slit 165 can be adjusted. In this way, when the brightness of the external environment has been changed, such as between the outdoor and the indoor, the light can be adjusted or shielded so as to be not too bright or too dark.

Thus, the present embodiment includes a detection window (opening) for sensing the internal optical state, whereby a display for brightness and operation confirmation can be presented, and the starting and stopping of the system side can be easily monitored.

The processing and controls may be implemented by software processing using a central processing unit (CPU) or a graphics processing unit (GPU), or by hardware processing using an application specific integrated circuit (ASIC) or a field programmable gate array (FPGA).

Using the device of the present invention makes it possible to revive functions that have degraded in the human brain. Concretely, according to the present invention, the amplitude of $\alpha$ waves and $\theta\theta$ waves being spontaneously generated is enhanced through the automatically adjusted pulsed light irradiation of the head centered around the prefrontal area (frontal association area) and on the basis of the rhythm of the brain waves unique to each individual, thereby non-invasively enhancing nervous impulse in the brain cortex, and achieving relaxation and activation of cellular immunity due to a change in the endocrine system.

During the process of human evolution, changes (evolution) in organs (including bones) occur to protect very important parts (particularly, from physical factors relating to survival). (It is believed that such is how the species and subspecies that exist today have evolved and been naturally selected to adapt to the environment). For the sake of evolution (in exchange for evolution), the functions that were originally in place relating to physiological stimulation or adjustment may have gradually degraded to no small extent. The present invention is a typical example of a technology for reviving the physiological and immunological functions that have had to be degraded.

According to the device of the present invention, the head of a human, particularly centered around the prefrontal area (frontal association area) is stimulated with red pulsed light of a specific wavelength region. In this way, the frequency or amplitude of $\alpha$ waves being disturbed by a distortion in the living organism beyond the scope of the rhythm (fluctuation) of the physiological phenomena are attuned with the frequency and amplitude between a part of a $\theta$-wave band and a part of the $\alpha$-wave band unique to each individual and then amplified, thereby improving and even preventing the distortion. The photic stimulation of the head causes revival of the degraded light-sensitive function in the brain surface (mainly the brain cortex). As a result, nerve cell excitement is promoted in the brain cortex, whereby an enhancement of nervous impulse takes place (with an associated reduction of mental stress, due to a change in the endocrine system), and the natural immune system (cellular immunity) is activated. This presumably leads to an enhancement of the immuno-surveillance capability to attack and defend against virus-infected cells or cancerous cells (of which three-thousand to five-thousand are said to be generated each day even in a healthy subject).

The immune system includes an acquired immune system and a natural immune system (cellular immunity). In the acquired immune system, when a foreign substance such as a bacteria or a virus has entered the body, antigen-presenting cells, such as dendritic cells, present an antigen to helper T cells to transmit information about the foreign substance, whereby the helper T cells instruct B cells to make an antibody against the antigen. The antibody attacks and destroys the foreign substance. On the other hand, the natural immune system (cellular immunity) is an immune system for an initial defense by NK cells, macrophages (phagocytes) and granulocytes (neutrophils), which patrol so that the foreign substance can be immediately attacked before the acquired immune system is activated. The photic stimulation of the head by the device of the present invention is characterized in that activation of NK cells is caused. An increase in the number of NK cells can be confirmed by measuring, by flow cytometry and the like, the abundance of the cells of $CD57^-CD16^+$ and $CD57^+CD16^+$ with respect to CD57 and CD16 (CD is an abbreviation of "Cluster of Differentiation"), which are cell surface antigens of NK cells in the peripheral blood.

It has been known that immunity can be increased by controlling the $\alpha$ waves of the human brain. In particular, activation of NK cells or the relaxation effect by photic stimulation using pulsed light with the frequency of 0.5 to 13 Hz have been described by the present inventor, for example, in JP H09-84888 A and JP 2001-231871 A, and by others. The technology, however, did not take individual differences (or differences among individuals) and predisposition into consideration, as discussed above, and instead involved irradiating the head with uniform light, resulting in the problem that the effect varies greatly among individuals. In human brain waves, $\alpha$ waves (frequency 13 to 8 Hz) appear when at rest and with closed eyes, and $\theta$ waves (frequency 7 to 4 Hz) appear during a shallow sleep. When awake, β waves (frequency 30 to 14 Hz) become dominant, and one is subject to the influence of nervousness or stress. The device of the present invention measures the brain waves of each individual and irradiates the head centered around the prefrontal area (frontal association area), for example, with red pulsed light (using an arbitrary wavelength region from 610 to 750 nm) which is automatically matched with the frequency and amplitude of the rhythm of the α waves unique to each individual. In this way, it becomes possible to enhance the amplitude of the brain waves between a part of a θ-wave band and a part of an α-wave band (normally 7 to 13 Hz; preferably 7 to 12 Hz and more preferably 7 to 10 Hz) that are being spontaneously generated. In fact, it has been confirmed that, by implementing the red pulsed light irradiation according to the present invention with respect to healthy subjects, cancer patients, the elderly and the like, in 1 to 6 sessions per day (for example, by a method whereby, in the case of 4 to 6 sessions per day, the first and second sessions are implemented with a "rest time (interval)" of 15 minutes or more in-between in the morning, and the same set of two sessions is also implemented once or twice in the afternoon), each session lasting for about 15 minutes, for 2 to 3 weeks or longer, the following can be achieved: enhancement of nervous impulse in the brain cortex (stimulation of the brain cortex function); activation of the living organism due to a change in the endocrine system (for example, a decrease in irritation or mental stress due to a decrease in the level of norepinephrine [noradrenaline] in the blood); and activation of the natural immune system (cellular immunity) (for example, an increase in NK cell activity).

By using the technology according to the present invention, it becomes possible to bring back the light sensitivity that originally existed in the brain surface (the part embryologically called telencephalon), thereby reviving parts of the physiological function that are being degraded in the brain of the modern man (for example, enhancement of nervous impulse in the brain cortex, activation of the living organism due to a change in the endocrine system, and activation of cellular immunity). Through the researches and studies done by the present inventor and others based on a coordination of medicine and science/technology, it has become possible to revive the light sensitivity of the brain cortex and to reinvigorate natural healing ability.

In the foregoing embodiments, the configurations and the like illustrated in the attached drawings are not limiting and may be modified, as appropriate, within the scope in which the effect of the present invention can be obtained. The embodiments may be modified and implemented without departing from the scope of the purpose of the present invention.

The constituent elements of the present invention may be optionally selected, and an invention provided with an optionally selected configuration is also included in the present invention.

INDUSTRIAL APPLICABILITY

The present invention may be utilized in a light pulse irradiation device for the head.

The present invention may be utilized in a photic stimulation device.

REFERENCE SIGNS LIST

1a Waveform generation unit
1-1 BPF unit
3 (PWM) pulse modulation unit
4 Light irradiation unit (LED)
11 Brain wave sensor
12 PLL (phase-locked loop) unit
13 Brain wave amplifier
15 FFT (Fourier transform) unit
17 Frequency and phase control unit
51 Cap-like member
51a Irradiating portion
51b Shield portion
53 Eye protection portion
57 Support plate
57a Exit hole All publications, patents and patent applications cited in the present description are incorporated herein by reference in their entirety.

The invention claimed is:

1. A head photic stimulation device comprising:
a brain wave amplifier which subjects a subject's brain waves acquired using a brain wave sensor to analog/digital (A/D) conversion and amplification;
a control signal generation circuit which, based on an output signal from the brain wave amplifier, generates control signal for controlling light emitting diode (LED) driving; and
a light irradiation unit which is driven based on an output from the control signal generation circuit, and which includes an LED in position for irradiating only a personal area of the head including the prefrontal area (frontal association area) of the head of the subject and excluding the occipital area,
a light irradiation output unit irradiating the head of the subject in the prefrontal area of the head, frontal association area, and
an eye protection portion arranged to protect the eyes of the subject from irradiation;
wherein:
the control signal generation circuit includes
a band-pass filter for filtering the output signal from the brain wave amplifier, and
a digital signal processing (DSP) unit for controlling the signal that has passed through the band-pass filter, and
the DSP unit includes
a feedback function for matching a phase of a pulse wave modulation (PWM) output for controlling the light irradiation output unit, in synchronism with the subject brain waves,
a fast Fourier transform (FFT) unit that extracts a frequency of a maximum amplitude of a part of a θ-wave band and a part of an α-wave band, and
a phased lock loop (PLL) that controls the phase of the signal output from the FFT unit, wherein the PLL includes: a phase comparator for comparing the phase of the input signal to a phase of the output signal of the PLL; a loop filter; and a voltage-controlled oscillator (VCO) which receives an output of the loop filter as an input and feeds an output of the VCO back to the phase comparator,
the band pass filter (BPF), and
the PLL synchronizes the phases of the output signal from the band-pass filter and output to the light irradiation unit controlled by the PWM, and
a frequency/phase control unit which controls the frequency and the phase of an input signal from the FFT unit and which performs the feedback to the PLL, and wherein the frequency/phase control unit, at a time of frequency switching, delays VCO output until an output phase of the output to the light irradiation unit becomes zero and, after an interval, performs synchronization in alignment with a zero point of a phase of input brain waves.

2. The head photic stimulation device according to claim 1, wherein the frequency/phase control unit synchronizes an amplitude in alignment with the phase of input brain wave at the time of frequency switching.

3. The head photic stimulation device according to claim 1, wherein the FFT unit extracts, from the part of the θ-wave band and the part of the α-wave band, the frequency of the maximum amplitude of the brain waves in the bands using the band-pass filter and the FFT, and further calculates a moving average to increase accuracy.

4. The head photic stimulation device according to claim 1, wherein
   the PLL performs a switching interrupt (pause) at a timing $t_1$,
   then, continues oscillation until a phase of the VCO reaches a zero-crossing point, and
   then, determines whether the phase of the PLL is zero, and, if zero, starts signal output of the PLL at a previous average frequency.

* * * * *